US012758513B2

(12) United States Patent
Lager et al.

(10) Patent No.: US 12,758,513 B2

(45) Date of Patent: Oct. 13, 2026

(54) CAPSAICIN DERIVATIVES IN THE TREATMENT OF IDIOPATHIC PULMONARY FIBROSIS

(71) Applicant: aXichem AB, Malmo (SE)

(72) Inventors: Erik Lager, Lund (SE); Lucas Altepost, Nesøya (NO); Torsten Helsing, Kleppestø (NO); Bomi Framroze, Menlo Park, CA (US)

( * ) Notice: Subject to any disclaimer, the term of this patent is extended or adjusted under 35 U.S.C. 154(b) by 367 days.

(21) Appl. No.: 18/564,031

(22) PCT Filed: Jun. 1, 2022

(86) PCT No.: PCT/EP2022/064876

§ 371 (c)(1),
(2) Date: Nov. 24, 2023

(87) PCT Pub. No.: WO2022/253884

PCT Pub. Date: Dec. 8, 2022

(65) Prior Publication Data

US 2024/0277637 A1 Aug. 22, 2024

(30) Foreign Application Priority Data

Jun. 2, 2021 (NO) .................................... 20210693

(51) Int. Cl.

| | |
|---|---|
| ***A61K 31/165*** | (2006.01) |
| ***A61K 31/235*** | (2006.01) |
| ***A61P 11/00*** | (2006.01) |

(52) U.S. Cl.

CPC .......... *A61K 31/165* (2013.01); *A61K 31/235* (2013.01); *A61P 11/00* (2018.01)

(58) Field of Classification Search

CPC .................................................... A61K 31/165

See application file for complete search history.

(56) References Cited

U.S. PATENT DOCUMENTS

2020/0354374 A1 11/2020 Pearce

FOREIGN PATENT DOCUMENTS

| | | | |
|---|---|---|---|
| WO | 2005025314 | A1 | 3/2005 |
| WO | WO2017160156 | * | 9/2017 |
| WO | 2020060914 | A1 | 3/2020 |
| WO | 2020160225 | A1 | 8/2020 |
| WO | 2020191501 | A1 | 10/2020 |
| WO | 2020259528 | A1 | 12/2020 |

OTHER PUBLICATIONS

International Search Report and Written Opinion for International Application No. PCT/EP2022/064876, mailing date of Oct. 19, 2022.

* cited by examiner

*Primary Examiner* — Rei Tsang Shiao

(74) *Attorney, Agent, or Firm* — Rivkin Radler LLP

(57) ABSTRACT

The present invention relates to the treatment of idiopathic pulmonary fibrosis. More particularly, the invention provides compounds, and compositions thereof, for use in methods for the treatment of idiopathic pulmonary fibrosis. The present invention also relates to a method for treatment of idiopathic pulmonary fibrosis, and to a method for inhibiting the activity of platelet-derived growth factor receptor (PDGF)-α and/or β in a subject in need thereof.

14 Claims, 3 Drawing Sheets

CAPSAICIN DERIVATIVES IN THE TREATMENT OF IDIOPATHIC PULMONARY FIBROSIS

FIELD OF THE INVENTION

The present invention relates to the treatment of idiopathic pulmonary fibrosis. More particularly, the invention provides compounds, and compositions thereof, for use in a method for the treatment of idiopathic pulmonary fibrosis. The present invention also relates to a method for treatment of idiopathic pulmonary fibrosis, and to a method for inhibiting the activity of platelet-derived growth factor receptor (PDGF)-α and/or β in a subject in need thereof.

BACKGROUND OF THE INVENTION

Idiopathic pulmonary fibrosis (IPF) belongs to the group of more than 200 lung diseases known as interstitial lung diseases (ILDs) or diffuse parenchymal lung disease (DPLDs), which affect the interstitium (the tissue and space around the alveoli). IPF is a chronic, progressive and ultimately fatal disease characterised by irreversible fibrosis of the lung parenchyma, with the fibrosis presenting in a usual interstitial pneumonia pattern and resulting loss of lung function. The alveoli of the patient become damaged and increasingly scarred, causing stiffness of the lungs and impaired gas exchange. The exact prevalence of IPF is unknown, but it is estimated that about 5 million people globally are affected by IPF, and that the disease newly occurs in about 12 per 100,000 people per year. Symptoms typically include a dry cough, fatigue, nail clubbing, aches, weight loss, and increasing dyspnea caused by low blood oxygen levels and the stiffness of the scar tissue.

With a clinical course that is variable and unpredictable, IPF has a prognosis that can be worse than for many cancers: IPF progression is associated with an estimated mean survival time of only about 2.5 to 5 years following definite diagnosis, and the 5-year survival for IPF ranges between 20 and 40%. Some patients have a rapid decline in lung function leading to death, while others experience a slower decline over time. Some show periods of clinical stability interspersed with episodes of rapid respiratory deterioration known as acute exacerbations, devastating events that may last for several days to weeks and from which recovery is extremely difficult. Acute exacerbations, though more common in patients with advanced lung function impairment, can occur at any time for IPF patients, and are associated with an in-hospital mortality estimated at over 50%.

Complications resulting from IPF include pulmonary hypertension, heart failure, pneumonia, and pulmonary embolism, in addition to respiratory failure. The deterioration in health-related quality of life of IPF patients is also associated with depression and anxiety.

There is currently no cure for IPF. Treatments are aimed at slowing down the progression of the disease and prolonging survival, relieving and reducing symptoms as much as possible, preventing acute exacerbations, and, as the condition becomes more advanced, palliative care. For a minority of patients, lung transplant is suitable, but donor lungs are scarce. Symptom management and supportive care, including oxygen treatment and pulmonary rehabilitation, are also important elements of the management of IPF. While some patients respond well to treatment, others get rapidly worse or find the breathlessness debilitating.

Two antifibrotic drugs, nintedanib and pirfenidone, have been approved for the treatment of IPF. These are recommended in the current (2015) treatment guidelines on IPF issued by the American Thoracic Society, European Respiratory Society, Japanese Respiratory Society, and Latin American Thoracic Association. The treatment guidelines also provide a conditional recommendation for the use of anti-acid therapy in patients with IPF and asymptomatic gastroesophageal reflux disease, but recommend against all other pharmacological therapies that have been used in the treatment of IPF, including the antioxidant N-acetylcysteine. Side effects for nintedanib and pirfenidone are common and substantial. Gastrointestinal side effects (nausea, diarrhoea, vomiting) are the most predominant for both therapies, with further side effects including rashes with pirfenidone and abnormal liver function with nintedanib. Neither pirfenidone nor nintedanib have been found to elevate patients' perceived quality of life.

A need therefore exists for new compounds and methods for the treatment of IPF.

BRIEF SUMMARY OF THE INVENTION

Figure 1:
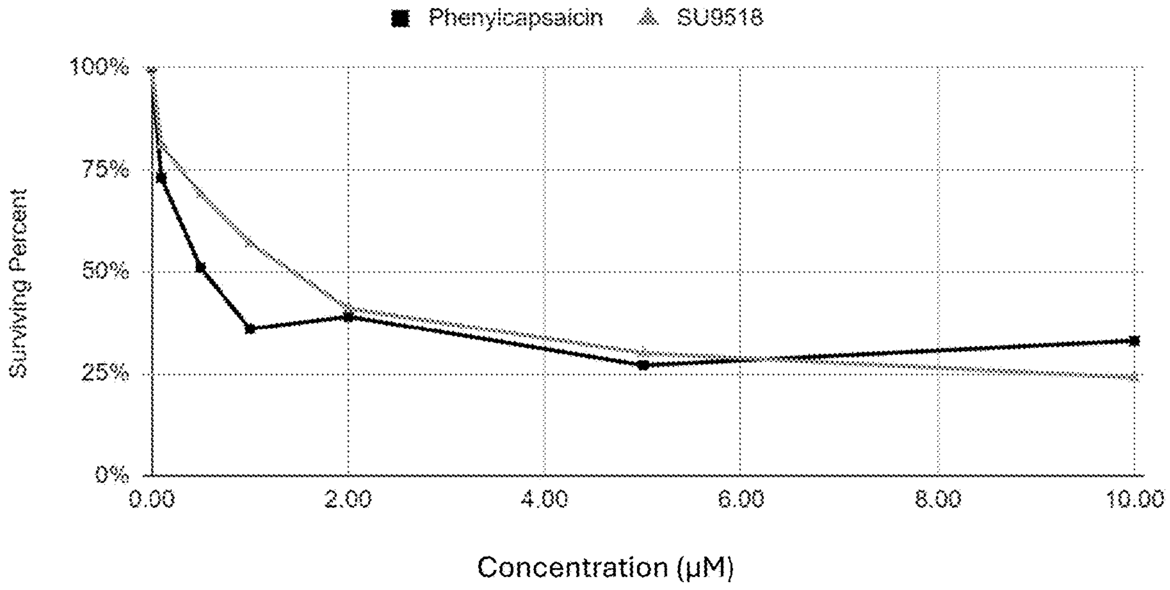
FIG. 1 shows the results from a clonogenic survival assay on survival of human corneal epithelial cells in the presence of PDGF.

The inventors have discovered that capsaicin derivatives of formula I represent a promising drug candidate against IPF.

In one aspect, the present invention relates to a compound of formula I, or a pharmaceutically acceptable salt or solvate thereof, for use in a method for the treatment of IPF,

I

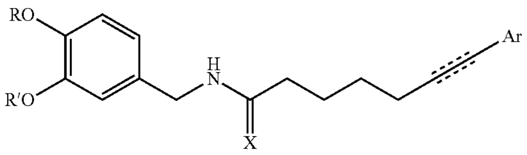

wherein

X is selected from oxygen and sulphur;

Ar denotes an aryl group optionally containing one or more nitrogen, oxygen, or sulphur atoms, and optionally substituted in any one or more positions with one or more identical or different substituents selected from the group comprising or consisting of fluoro; chloro; bromo; iodo, cyano, nitro, trifluoromethyl, $C_1$-$C_6$ straight chain and branched alkoxy, $C_1$-$C_6$ sulfoxy, —S—$C_1$-$C_6$ alkyl, $C_1$-$C_6$ straight chain and branched alkyl, $C_2$-$C_6$ straight chain and branched alkenyl, $C_2$-$C_6$ straight chain and branched alkynyl, $C_1$-$C_6$ fluoroalkyl, chloroalkyl, bromoalkyl, and iodoalkyl, COO—$C_1$-$C_6$ alkyl, N($C_1$-$C_6$ alkyl)$_2$ and CON($C_1$-$C_6$ alkyl)$_2$; and R' is selected from the group comprising or consisting of hydrogen, $C_1$-$C_6$ straight chain or branched alkyl, and $C_3$-$C_6$ cycloalkyl;

R is selected from the group comprising or consisting of hydrogen; benzyl; $C_1$-$C_{18}$ straight chain and branched alkyl, alkenyl, and alkynyl; $C_3$-$C_6$ cycloalkyl; acyl groups $COR^1$ wherein $R^1$ is selected from the group comprising or consisting of $C_1$-$C_{18}$ straight chain and branched alkyl, alkenyl, and alkynyl, $C_3$-$C_6$ cycloalkyl, phenyl; and substituted phenyl wherein the phenyl ring is substituted in any one or more positions with 1-5 identical or different substituents selected from the group consisting of fluoro, chloro, bromo, iodo, cyano, nitro, trifluoromethyl, $C_1$-$C_6$ straight chain and branched alkoxy, $C_1$-$C_6$ sulfoxy, —S—$C_1$-$C_6$ alkyl, $C_1$-$C_6$ straight chain and branched alkyl, $C_2$-$C_6$ straight chain and branched alkenyl, $C_2$-$C_6$ straight chain and branched alkynyl, $C_1$-$C_6$ fluoroalkyl, chloroalkyl, bromoalkyl, and iodoalkyl, COO—$C_1$-$C_6$ alkyl, and CON ($C_1$-$C_6$ alkyl)$_2$; sulfamate esters ($SO_2NH_2$); acyl groups of naturally occurring amino acids; acyl groups of five-membered cyclic amino acid esters (amino group in 2 or 3 position); acyl groups of six-membered cyclic amino acid esters (amino group in 2, 3, or 4 position); $CONR^3R^4$ wherein $R^3$ and $R^4$ each independently is selected from $C_1$-$C_{18}$ straight chain and branched alkyl, alkenyl, and alkynyl and $C_3$-$C_6$ cycloalkyl; phosphate esters $PO_3^{2-}$ having counter ions selected from $Ca^{2+}$, $Na^+$, and $K^+$; phosphate esters $PO_3H^-$ having counter ions selected from $Ca^{2+}$, $Na^+$, and $K^+$; $CO(CH)_2COOH$; $CO(CH_2)_2COOH$; and $CO(CH_2)_3COOH$, and the bond between the carbon atom in a position to the aryl group and the carbon atom in β position to the aryl group is a single bond, a double bond, or a triple bond.

In one embodiment, the invention provides a compound of formula II, or a pharmaceutically acceptable salt or solvate thereof, for use in a method for the treatment of IPF,

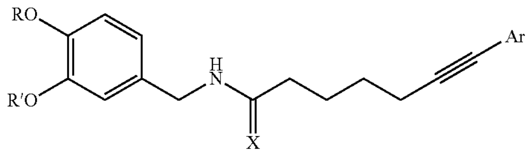

II wherein

X is selected from oxygen and sulphur;

Ar denotes an aryl group optionally containing one or more nitrogen, oxygen, or sulphur atoms, and optionally substituted in any one or more positions with one or more identical or different substituents selected from the group comprising or consisting of nitro, trifluoromethyl, $C_1$-$C_6$ straight chain and branched alkoxy, $C_1$-$C_6$ straight chain and branched alkyl; and R' is selected from the group comprising or consisting of hydrogen, and $C_1$-$C_6$ straight chain or branched alkyl;

R is selected from the group comprising or consisting of hydrogen; $C_1$-$C_6$ straight chain and branched alkyl, alkenyl, and alkynyl; $C_3$-$C_6$ cycloalkyl; acyl groups $COR^1$ wherein $R^1$ is selected from the group comprising or consisting of $C_1$-$C_6$ straight chain and branched alkyl, alkenyl, and alkynyl, $C_3$-$C_6$ cycloalkyl and phenyl.

These compounds have been found by the inventors to exhibit a dose-dependent inhibitory effect on survival of human bronchial epithelial cells in the presence of PDGF (platelet-derived growth factor receptors), considerably lowering the survival rate of the cells. These results are a strong indication of the usefulness of the compounds in the treatment of IPF.

In another aspect, the invention relates to a composition comprising such compound or pharmaceutically acceptable salt or solvate thereof for use in a method for the treatment of IPF.

In another aspect, the invention relates to a kit comprising said compound or composition and an inhaler.

DETAILED DESCRIPTION OF THE INVENTION

Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art.

The term "derivative" as used herein refers to a molecule that differs in chemical structure from a parent compound. Examples of derivatives include, without limitation: homologues, which differ incrementally from the chemical structure of the parent, such as a difference in the length of an aliphatic chain; molecular fragments; structures that differ by one or more functional groups from the parent compound, such as can be made by transforming one or more functional groups of a parent; a change in ionization state of a parent, such as ionising an acid to its conjugate base; isomers, including positional, geometric and stereoisomers; and combinations thereof.

As will be understood, any of the compounds herein described may be provided in the form of a pharmaceutically acceptable salt or solvate thereof, such as a hydrate thereof. Procedures for salt formation and solvate formation are conventional in the art.

The terms "treating" and "treatment" and "therapy" (and grammatical variations thereof) are used herein interchangeably, and refer to 1) inhibiting the disease; for example, inhibiting a disease, condition or disorder in a subject who is experiencing or displaying the pathology or symptomatology of the disease, condition or disorder, including prevention of disease (i.e. prophylactic treatment, arresting further development of the pathology and/or symptomatology), or 2) alleviating the symptoms of the disease, or 3) ameliorating the disease; for example, ameliorating a disease, condition or disorder in an subject who is experiencing or displaying the pathology or symptomatology of the disease, condition or disorder (i.e., reversing the pathology and/or symptomatology). The terms may relate to the use and/or administration of medicaments, active pharmaceutical ingredients (API), food additives, food supplements, dietary supplements, nutritional supplements, over-the-counter (OTC) supplements, medical foods, and/or a pharmaceutical grade supplements.

Since the initial stages of IPF were long thought to mainly involve chronic inflammation, corticosteroids and other anti-inflammatory and/or immunosuppressive drugs were used in the treatment of IPF. However, over the last years there has been a conceptual transition in IPF pathogenesis from an inflammatory driven process to a primarily fibrotic one, in which fibrogenesis results from recurrent microinjury of alveolar epithelial cells followed by aberrant repair processes leading to fibrosis. Hence, agents targeting persistent fibrosis resulting from aberrant repair of alveolar epithelial injury have been in the spotlight, and there has also been an increase in the number of available antifibrotic treatment options, starting with pirfenidone and nintedanib. Pirfenidone helps to slow the development of scarring in the lungs by reducing the activity of the immune system. Nintedanib is a newer medicine that can also help slow down scarring of the lungs in some IPF patients. Both have been shown in clinical trials to slow progression of mild-to-moderate idiopathic pulmonary fibrosis. However, as mentioned above, both drugs show considerable side effects. N-acetylcysteine has also found some use in the treatment of IPF, with some studies suggesting that it may reduce the amount of scar tissue in the lungs. Other studies have not shown any benefit, and N-acetylcysteine is now widely discouraged.

The etiology and exact pathophysiological mechanism of IPF have not yet been fully elucidated. The prevailing theory is that IPF is caused by persistent alveolar epithelial cell micro-injury combined with a dysregulated repair process.

The naturally occurring alkaloid capsaicin (1) and other structurally related compounds, including the synthetic phenylcapsaicin (2) (N-(4-hydroxy-3-methoxybenzyl)-7-phenylhept-6-ynamide) and derivatives thereof, have found use in various areas. Phenylcapsaicin has been shown to have low systemic toxicity and to be safe with regards to gene mutations and chromosomal damage (Rage Paulsen et al., *Toxicology Research and Application* 2018, 2, 1), and has been examined by the European Food Safety Authority and regarded as safe (EFSA NDA Panel et al., *EFSA Journal* 2019, 17(6), e05718).

1

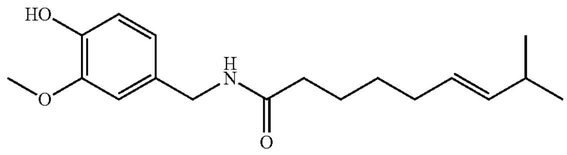

2

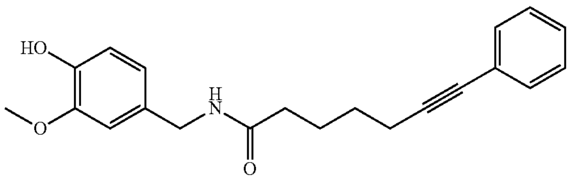

Both capsaicin and phenylcapsaicin are known TRPV1 agonists. As TRPV1 is overexpressed in IPF, cough sensitivity to inhaled capsaicin is known to be significantly increased in IPF patients. Capsaicin has therefore been used in studies of the pathogenesis of cough in IPF. The use of capsaicin has also been suggested for use in cough prevention in patients with chronic cough, or in the release of symptoms in various diseases including respiratory diseases such as pulmonary fibrosis, but has not found widespread use.

The inventors have found that compounds of structure I represent a very promising drug candidate for the treatment of IPF. In clonogenic cell survival assays of human bronchial epithelial cells (Examples 2 and 3), phenylcapsaicin was surprisingly found to exhibit a dose-dependent inhibitory effect on survival of human bronchial epithelial cells in the presence of PDGF (platelet-derived growth factor receptors), lowering the survival rate of the cells to only 35% after 14 days in the presence of 10 μM of phenylcapsaicin. These findings strongly imply that phenylcapsaicin may be a useful drug against IPF, slowing down or reducing scarring of the lung tissue. Such a reduction in scarring may lead to a delayed progression of IPF and/or ease the symptoms of IPF, such as respiratory difficulty and/or coughing. Further, it has been found in an acute inhalation toxicity test on rats (single exposure via inhalation, nose-only exposure) that $LC_{50}$ of phenylcapsaicin is greater than 5.65 mg/L in male and female rats based on active substance. This finding is an indication that the compounds of the invention will have a low toxicity in use against IPF using inhalation as the route of administration.

Interestingly, in a corresponding clonogenic cell survival assay (Example 3), capsaicin showed hardly any effect at all, with 95% survival at 10 μM of capsaicin, while phenylcapsaicin lowered survival to 83% at only 0.10 μM and to a mere 32% at 10 μM. Other structurally similar compounds tested in the same assay indicate that the presence of an aromatic ring in the side chain has importance: Replacing the alkynyl benzene phenyl ring of phenylcapsaicin with a saturated cyclohexyl ring (compound 3) lowered activity considerably (73% survival at 10 μM), while the tert-butyl derivative (compound 4) had only a slight activity in this assay (91% survival at 10 μM). Further, it was found that derivatisation of the hydroxy group of the vanillyl group to form an acetoxy group improved the effect; the acetoxy derivative of phenylcapsaicin (compound 5) reduced survival to only 20% at 10 μM. The corresponding acetoxy derivative of compound 3 (compound 6) also gave better results than compound 3, but the introduction of an acetoxy group in compound 4 (compound 7) could not mediate the negative effects of the tert-butyl group.

3

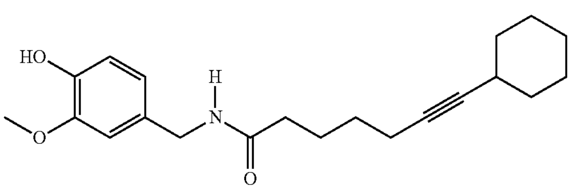

4

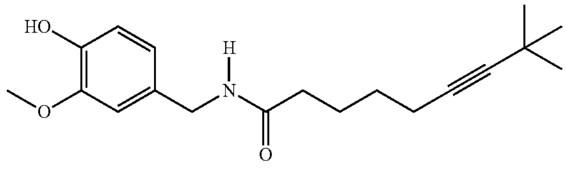

5

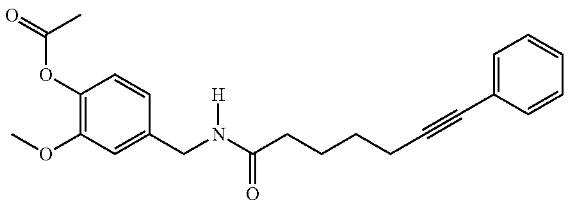

-continued

6

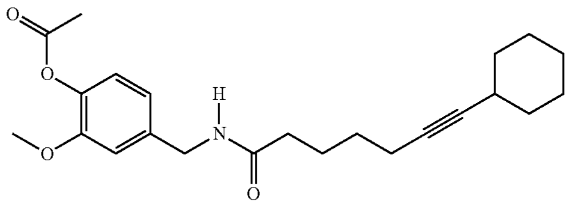

7

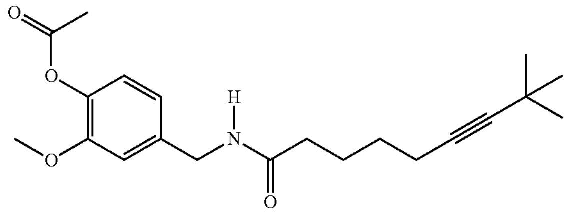

Furthermore, compound 10, the 4-nitrophenyl analog of phenylcapsaicin, and compound 12, the naphthalene analog of phenylcapsaicin, showed similar cell survival percent as the parent phenylcapsaicin. Compound 11, the 4-methoxyphenyl analog of phenylcapsaicin, showed a higher reduction than the lead phenylcapsaicin in the cell survival study.

10

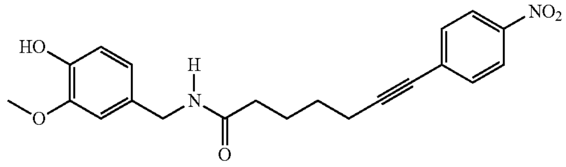

11

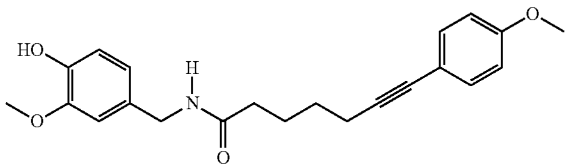

12

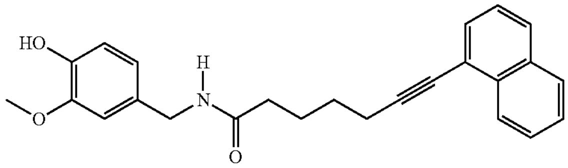

Although not wishing to be bound by any theory relating to their mechanism of action, a possible explanation for the observed effect of the compounds of the invention is that the compounds act as a competitive inhibitor of platelet-derived growth factor receptors (PDGF)-α and β. PDGF has been shown in the literature to be a profibrotic mediator and to play an important role in the pathogenesis of IPF, and it has been shown that inhibition of platelet-derived growth factor signalling attenuates pulmonary fibrosis. The effect of the compounds according to the invention on IPF may be explained by them being effective PDGF inhibitors, as indicated by the results from Examples 2, 3 and 4.

In one aspect, the invention provides a compound of formula I, or a pharmaceutically acceptable salt or solvate thereof, for use in a method for the treatment of an ILD, preferably an idiopathic ILD and/or a pulmonary fibrosis, more preferably IPF. In some embodiments, the invention provides a compound of formula I, or a pharmaceutically acceptable salt or solvate thereof, for use in a method for the treatment of IPF. As used herein, the term "pharmaceutically acceptable" means that compound must be physiologically acceptable to the recipient as well as, if part of a composition, compatible with other ingredients of the composition.

I

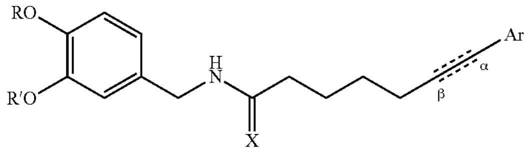

The dotted lines indicated the optional presence of a bond, meaning that the bond between the carbon atom in a position to the aryl group and the carbon atom in β position to the aryl group, from now on referred to as "the α-β bond", may be a single bond, a double bond, or a triple bond.

In some embodiments, in said compound of formula I, the α-β bond is selected from a single bond, a double bond, and a triple bond;

X is selected from oxygen and sulphur;

Ar denotes an aryl group optionally containing one or more nitrogen, oxygen, or sulphur atoms, and optionally substituted in any one or more positions with one or more identical or different substituents selected from the group comprising or consisting of fluoro; chloro; bromo; iodo, cyano, nitro, trifluoromethyl, $C_1$-$C_6$ straight chain and branched alkoxy, $C_1$-$C_6$ sulfoxy, —S—$C_1$-$C_6$ alkyl, $C_1$-$C_6$ straight chain and branched alkyl, $C_2$-$C_6$ straight chain and branched alkenyl, $C_2$-$C_6$ straight chain and branched alkynyl, $C_1$-$C_6$ fluoroalkyl, chloroalkyl, bromoalkyl, and iodoalkyl, COO—$C_1$-$C_6$ alkyl, $N(C_1$-$C_6\ alkyl)_2$ and $CON(C_1$-$C_6\ alkyl)_2$;

R' is selected from the group comprising or consisting of hydrogen, $C_1$-$C_6$ straight chain or branched alkyl, and $C_3$-$C_6$ cycloalkyl; and R is selected from the group comprising or consisting of hydrogen; benzyl; $C_1$-$C_{18}$ straight chain and branched alkyl, alkenyl, and alkynyl; $C_3$-$C_6$ cycloalkyl; optionally substituted phenyl groups; acyl groups $COR^1$ wherein $R^1$ is selected from the group comprising or consisting of straight chain, branched and cyclic alkyl; sulfamate esters ($SO_2NH_2$); acyl groups of naturally occurring amino acids; acyl groups of five-membered cyclic amino acid esters (amino group in 2 or 3 position); acyl groups of six-membered cyclic amino acid esters (amino group in 2, 3, or 4 position); $CONR^3R^4$ wherein $R^3$ and $R^4$ each independently is straight chain, branched, and cyclic alkyl, alkenyl, and alkynyl; phosphate esters $PO_3^{2-}$ having counter ions selected from $Ca^{2+}$, $Na^+$, and $K^+$; phosphate esters $PO_3H^-$ having counter ions selected from $Ca^{2+}$, $Na^+$, and $K^+$; $CO(CH)_2COOH$; $CO(CH_2)_2COOH$; and $CO(CH_2)_3COOH$.

Preferably, in said compound of formula I, the α-β bond is selected from a single bond, a double bond, and a triple bond, and is most preferably a triple bond;

X is selected from oxygen and sulphur;

Ar denotes an aryl group optionally containing one or more nitrogen, oxygen, or sulphur atoms, and optionally substituted in any one or more positions with one or more identical or different substituents selected from the group comprising or consisting of fluoro; chloro; bromo; iodo, cyano, nitro, trifluoromethyl, $C_1$-$C_6$ straight chain and branched alkoxy, $C_1$-$C_6$ sulfoxy, —S—$C_1$-$C_6$ alkyl, $C_1$-$C_6$ straight chain and branched alkyl, $C_2$-$C_6$ straight chain and branched alkenyl, $C_2$-$C_6$ straight chain and branched alkynyl, $C_1$-$C_6$ fluoroalkyl, chloroalkyl, bromoalkyl, and iodoalkyl, COO—$C_1$-$C_6$ alkyl, N($C_1$-$C_6$ alkyl)$_2$ and CON($C_1$-$C_6$ alkyl)$_2$;

R' is selected from the group comprising or consisting of hydrogen, $C_1$-$C_6$ straight chain or branched alkyl, and $C_3$-$C_6$ cycloalkyl; and R is selected from the group comprising or consisting of hydrogen; benzyl; $C_1$-$C_{18}$ straight chain and branched alkyl, alkenyl, and alkynyl; $C_3$-$C_6$ cycloalkyl; acyl groups $COR^1$ wherein $R^1$ is selected from the group comprising or consisting of $C_1$-$C_{18}$ straight chain and branched alkyl, alkenyl, and alkynyl, $C_3$-$C_6$ cycloalkyl, phenyl; and substituted phenyl wherein the phenyl ring is substituted in any one or more positions with 1-5 identical or different substituents selected from the group consisting of fluoro, chloro, bromo, iodo, cyano, nitro, trifluoromethyl, $C_1$-$C_6$ straight chain and branched alkoxy, $C_1$-$C_6$ sulfoxy, —S—$C_1$-$C_6$ alkyl, $C_1$-$C_6$ straight chain and branched alkyl, $C_2$-$C_6$ straight chain and branched alkenyl, $C_2$-$C_6$ straight chain and branched alkynyl, $C_1$-$C_6$ fluoroalkyl, chloroalkyl, bromoalkyl, and iodoalkyl, COO—$C_1$-$C_6$ alkyl, and CON ($C_1$-$C_6$ alkyl)$_2$; sulfamate esters ($SO_2NH_2$); acyl groups of naturally occurring amino acids; acyl groups of five-membered cyclic amino acid esters (amino group in 2 or 3 position); acyl groups of six-membered cyclic amino acid esters (amino group in 2, 3, or 4 position); $CONR^3R^4$ wherein $R^3$ and $R^4$ each independently is selected from $C_1$-$C_{18}$ straight chain and branched alkyl, alkenyl, and alkynyl and $C_3$-$C_6$ cycloalkyl; phosphate esters $PO_3^{2-}$ having counter ions selected from $Ca^{2+}$, $Na^+$, and $K^+$; phosphate esters $PO_3H^-$ having counter ions selected from $Ca^{2+}$, $Na^+$, and $K^+$; CO $(CH)_2COOH$; $CO(CH_2)_2COOH$; and $CO(CH_2)_3$ COOH.

In some embodiments, in said compound of formula I, the α-s bond is a triple bond;

X is selected from oxygen and sulphur;

Ar denotes an aryl group optionally containing one or more nitrogen, oxygen, or sulphur atoms, and optionally substituted in any one or more positions with one or more identical or different substituents selected from the group comprising or consisting of fluoro; chloro; bromo; iodo, cyano, nitro, trifluoromethyl, $C_1$-$C_6$ straight chain and branched alkoxy, $C_1$-$C_6$ sulfoxy, —S—$C_1$-$C_6$ alkyl, $C_1$-$C_6$ straight chain and branched alkyl, $C_2$-$C_6$ straight chain and branched alkenyl, $C_2$-$C_6$ straight chain and branched alkynyl, $C_1$-$C_6$ fluoroalkyl, chloroalkyl, bromoalkyl, and iodoalkyl, COO—$C_1$-$C_6$ alkyl, N($C_1$-$C_6$ alkyl)$_2$, and CON($C_1$-$C_6$ alkyl)$_2$, more preferably Ar denotes an aryl group optionally containing one or more nitrogen, oxygen, or sulphur atoms, and optionally substituted in any one or more positions with one or more identical or different substituents selected from the group comprising or consisting of nitro, trifluoromethyl, $C_1$-$C_6$ straight chain and branched alkoxy, $C_1$-$C_6$ straight chain and branched alkyl; and R' is selected from the group comprising or consisting of hydrogen, $C_1$-$C_6$ straight chain or branched alkyl, and $C_3$-$C_6$ cycloalkyl, and is more preferably selected from the group of hydrogen and $C_1$-$C_6$ straight chain or branched alkyl; and R is selected from the group comprising or consisting of hydrogen; benzyl; $C_1$-$C_{18}$ straight chain and branched alkyl, alkenyl, and alkynyl; $C_3$-$C_6$ cycloalkyl; acyl groups $COR^1$ wherein $R^1$ is selected from the group comprising or consisting of $C_1$-$C_{18}$ straight chain and branched alkyl, alkenyl, and alkynyl, $C_3$-$C_6$ cycloalkyl, phenyl; and substituted phenyl wherein the phenyl ring is substituted in any one or more positions with 1-5 identical or different substituents selected from the group consisting of fluoro, chloro, bromo, iodo, cyano, nitro, trifluoromethyl, $C_1$-$C_6$ straight chain and branched alkoxy, $C_1$-$C_6$ sulfoxy, —S—$C_1$-$C_6$ alkyl, $C_1$-$C_6$ straight chain and branched alkyl, $C_2$-$C_6$ straight chain and branched alkenyl, $C_2$-$C_6$ straight chain and branched alkynyl, $C_1$-$C_6$ fluoroalkyl, chloroalkyl, bromoalkyl, and iodoalkyl, COO—$C_1$-$C_6$ alkyl, and CON ($C_1$-$C_6$ alkyl)$_2$; sulfamate esters ($SO_2NH_2$); acyl groups of naturally occurring amino acids; acyl groups of five-membered cyclic amino acid esters (amino group in 2 or 3 position); acyl groups of six-membered cyclic amino acid esters (amino group in 2, 3, or 4 position); $CONR^3R^4$ wherein $R^3$ and $R^4$ each independently is selected from $C_1$-$C_{18}$ straight chain and branched alkyl, alkenyl, and alkynyl and $C_3$-$C_6$ cycloalkyl; phosphate esters $PO_3^{2-}$ having counter ions selected from $Ca^{2+}$, $Na^+$, and $K^+$; phosphate esters $PO_3H^-$ having counter ions selected from $Ca^{2+}$, $Na^+$, and $K^+$; $CO(CH)_2$ COOH; $CO(CH_2)_2COOH$; and $CO(CH_2)_3COOH$, and more preferably R is selected from the group of hydrogen; $C_1$-$C_6$ straight chain and branched alkyl, alkenyl, and alkynyl; $C_3$-$C_6$ cycloalkyl; acyl groups $COR^1$ wherein $R^1$ is selected from the group comprising or consisting of $C_1$-$C_6$ straight chain and branched alkyl, alkenyl, and alkynyl, $C_3$-$C_6$ cycloalkyl and phenyl.

In some embodiments, in said compound of formula I, the α-β bond is selected from a single bond, a double bond, and a triple bond;

X is selected from oxygen and sulphur;

Ar denotes a phenyl group or a naphthyl group optionally containing one or more nitrogen, oxygen, or sulphur atoms, and optionally substituted in any one or more positions with one or more identical or different substituents selected from the group comprising or consisting of fluoro; chloro; bromo; iodo, cyano, nitro, trifluoromethyl, $C_1$-$C_6$ straight chain and branched alkoxy, $C_1$-$C_6$ sulfoxy, —S—$C_1$-$C_6$ alkyl, $C_1$-$C_6$ straight chain and branched alkyl, $C_2$-$C_6$ straight chain and branched alkenyl, $C_2$-$C_6$ straight chain and branched alkynyl, $C_1$-$C_6$ fluoroalkyl, chloroalkyl, bromoalkyl, and iodoalkyl, COO—$C_1$-$C_6$ alkyl, N($C_1$-$C_6$ alkyl)$_2$, and CON($C_1$-$C_6$ alkyl)$_2$; and R' is selected from the group comprising or consisting of hydrogen, $C_1$-$C_6$ straight chain or branched alkyl, and $C_3$-$C_6$ cycloalkyl; and R is selected from the group comprising or consisting of hydrogen; benzyl; $C_1$-$C_8$ straight chain and branched alkyl, alkenyl, and alkynyl; $C_3$-$C_6$ cycloalkyl; acyl groups $COR^1$ wherein $R^1$ is selected from the group comprising or consisting of $C_1$-$C_8$ straight chain and branched alkyl, alkenyl, and alkynyl, $C_3$-$C_6$ cycloalkyl, and phenyl; sulfamate esters ($SO_2NH_2$); acyl groups of naturally occurring amino acids; acyl groups of five-membered cyclic amino acid esters (amino group in 2 or 3 position); acyl groups of six-membered cyclic amino acid esters (amino group in 2, 3, or 4 position); $CONR^3R^4$ wherein $R^3$ and $R^4$ each independently is selected from $C_1$-$C_8$ straight chain and branched alkyl, alkenyl, and alkynyl and $C_3$-$C_6$ cycloalkyl; phosphate esters $PO_3^{2-}$ having counter ions selected from $Ca^{2+}$, $Na^+$, and $K^+$; phosphate esters $PO_3H^-$ having counter ions selected from $Ca^{2+}$, $Na^+$, and $K^+$; $CO(CH)_2COOH$; $CO(CH_2)_2COOH$; and $CO(CH_2)_3COOH$.

According to the invention, the α-β bond, X, Ar, R, and R' may be varied and combined in different ways, resulting in a range of compounds that all fall within the general formula I, and that all may be useful, either as such or as a pharmaceutically acceptable salt or solvate thereof, in the treatment of IPF.

The aryl ring may be an aryl ring without any heteroatoms. Such variants are denoted a1.

The aryl ring may be a phenyl ring or a naphthyl ring without any heteroatoms. Such variants are denoted a2.

The aryl ring may be a phenyl ring without any heteroatoms. Such variants are denoted a3.

The aryl ring may be an aryl ring containing one or more nitrogen, oxygen, or sulphur atoms. Such variants are denoted a4.

The aryl ring may be a phenyl ring or a naphthyl ring containing one or more nitrogen, oxygen, or sulphur atoms. Such variants are denoted a5.

The aryl ring may be a phenyl ring containing one or more nitrogen, oxygen, or sulphur atoms. Such variants are denoted a6.

The aryl ring may be substituted in from one to all positions with identical or different substituents selected from the group comprising or consisting of fluoro; chloro; bromo; iodo; cyano; nitro; trifluoromethyl; $C_1$-$C_6$ straight chain and branched alkoxy; $C_1$-$C_6$ sulfoxy; —S—$C_1$-$C_6$ alkyl; $C_1$-$C_{12}$ straight chain and branched alkyl, alkenyl, and alkynyl; $C_1$-$C_6$ fluoroalkyl, chloroalkyl, bromoalkyl, and iodoalkyl; COO—$C_1$-$C_6$ alkyl; $N(C_1$-$C_6$ alkyl$)_2$; and CON($C_1$-$C_6$ alkyl$)_2$. Such variants are denoted b1.

The aryl ring may be substituted in from one to all positions with identical or different substituents selected from the group comprising or consisting of fluoro; chloro; bromo; iodo; cyano; nitro; trifluoromethyl; $C_1$-$C_6$ straight chain and branched alkoxy; $C_1$-$C_6$ sulfoxy; —S—$C_1$-$C_6$ alkyl; $C_1$-$C_{12}$ straight chain and branched alkyl, alkenyl, and alkynyl; and $C_1$-$C_6$ fluoroalkyl, chloroalkyl, bromoalkyl, and iodoalkyl. Such variants are denoted b2.

The aryl ring may be substituted in from one to all positions with identical or different substituents selected from the group comprising or consisting of fluoro; chloro; bromo; iodo; cyano; nitro; and trifluoromethyl. Such variants are denoted b3.

The aryl ring may be substituted in from one to all positions with identical or different substituents selected from the group comprising or consisting of fluoro; chloro; bromo; iodo; $C_1$-$C_{12}$ straight chain and branched alkyl, alkenyl, and alkynyl; $N(C_1$-$C_6$ alkyl$)_2$, and $C_1$-$C_6$ straight chain and branched alkoxy. Such variants are denoted b4.

The aryl ring may be substituted in from one to all positions with identical or different substituents selected from the group comprising or consisting of fluoro; chloro; bromo; iodo; $C_1$-$C_6$ straight chain and branched alkyl, alkenyl, and alkynyl; and $C_1$-$C_4$ straight chain and branched alkoxy. Such variants are denoted b5.

The aryl ring may be substituted in from one to all positions with identical or different substituents selected from the group comprising or consisting of nitro; $C_1$-$C_6$ straight chain and branched alkyl, alkenyl, and alkynyl; $N(C_1$-$C_6$ alkyl$)_2$, and $C_1$-$C_4$ straight chain and branched alkoxy. Such variants are denoted b6.

The aryl ring may be unsubstituted. Such variants are denoted b7.

In some variants, two substituents on the aryl ring are identical to each other. In some variants, three of the substituents are identical to each other. In some variants, four of the substituents are identical to each other. In some variants, five or more of the substituents are identical to each other. In other variants, all of said substituents are different from each other.

All variants a1-a6 may be combined with all variants b1-b7, giving a range of aryl groups optionally containing a heteroatom and optionally being substituted, resulting in the following Ar groups:

ArI=a1+b1, ArII=a1+b2, ArIII=a1+b3, ArIV=a1+b4, ArV=a1+b5, ArVI=a1+b6, ArVII=a1+b7, ArVII=a2+b1, ArIX=a2+b2, ArX=a2+b3, ArXI=a2+b4, ArXII=a2+b5, ArXIII=a2+b6, ArXIV=a2+b7, ArXV=a3+b1, ArXVI=a3+b2, ArXVII=a3+b3, ArXVIII=a3+b4, ArXIX=a3+b5, ArXX=a3+b6, ArXXI=a3+b7, ArXXII=a4+b1, ArXXIII=a4+b2, ArXXIV=a4+b3, ArXXV=a4+b4, ArXXVI=a4+b5, ArXXVII=a4+b6, ArXXVIII=a4+b7, ArXXIX=a5+b1, ArXXX=a5+b2, ArXXXI=a5+b3, ArXXXII=a5+b4, ArXXXIII=a5+b5, ArXXXIV=a5+b6, ArXXXV=a5+b7, ArXXXVI=a6+b1, ArXXXVII=a6+b2, ArXXXVIII=a6+b3, ArXXXIX=a6+b4, ArXXXX=a6+b5, ArXXXXI=a6+b6, ArXXXXII=a6+b7.

The letter-number combinations refer to the variants defined above, so that e.g. a1+b1 means that the aryl ring is an aryl ring without any heteroatoms (a1), that is substituted in from one to all positions with identical or different substituents selected from the group comprising or consisting of fluoro; chloro; bromo; iodo; cyano; nitro; trifluoromethyl; $C_1$-$C_6$ straight chain and branched alkoxy; $C_1$-$C_6$ sulfoxy; —S—$C_1$-$C_6$ alkyl; $C_1$-$C_{12}$ straight chain and branched alkyl, alkenyl, and alkynyl; $C_1$-$C_6$ fluoroalkyl, chloroalkyl, bromoalkyl, and iodoalkyl; COO—$C_1$-$C_6$ alkyl; $N(C_1$-$C_6$ alkyl$)_2$; and CON($C_1$-$C_5$ alkyl$)_2$ (b1), and a6+b7 means a phenyl ring containing one or more nitrogen, oxygen, or sulphur atoms (a6), that is unsubstituted (b7), and so on.

R' may selected from the group comprising or consisting of hydrogen, $C_1$-$C_6$ straight chain or branched alkyl, and $C_3$-$C_6$ cycloalkyl; and R may be selected from the group comprising or consisting of hydrogen; benzyl; $C_1$-$C_{18}$ straight chain and branched alkyl, alkenyl, and alkynyl; $C_3$-$C_6$ cycloalkyl; acyl groups $COR^1$ wherein $R^1$ is selected from the group comprising or consisting of $C_1$-$C_{18}$ straight chain and branched alkyl, alkenyl, and alkynyl, $C_3$-$C_6$ cycloalkyl, phenyl; and substituted phenyl wherein the phenyl ring is substituted in any one or more positions with 1-5 identical or different substituents selected from the group consisting of fluoro, chloro, bromo, iodo, cyano, nitro, trifluoromethyl, $C_1$-$C_6$ straight chain and branched alkoxy, $C_1$-$C_6$ sulfoxy, —S—$C_1$-$C_6$ alkyl, $C_1$-$C_6$ straight chain and branched alkyl, $C_2$-$C_6$ straight chain and branched alkenyl, $C_2$-$C_6$ straight chain and branched alkynyl, $C_1$-$C_6$ fluoroalkyl, chloroalkyl, bromoalkyl, and iodoalkyl, COO—$C_1$-$C_6$ alkyl, and CON($C_1$-$C_6$ alkyl$)_2$; sulfamate esters ($SO_2NH_2$); acyl groups of naturally occurring amino acids; acyl groups of five-membered cyclic amino acid esters (amino group in 2 or 3 position); acyl groups of six-membered cyclic amino acid esters (amino group in 2, 3, or 4 position); $CONR^3R^4$ wherein $R^3$ and $R^4$ each independently is selected from $C_1$-$C_{18}$ straight chain and branched alkyl, alkenyl, and alkynyl and $C_3$-$C_6$ cycloalkyl; phosphate esters $PO_3^{2-}$ having counter ions selected from $Ca^{2+}$, $Na^+$, and $K^+$; phosphate esters $PO_3H^-$ having counter ions selected from $Ca^{2+}$, $Na^+$, and $K^+$; $CO(CH)_2COOH$; $CO(CH_2)_2COOH$; and $CO(CH_2)_3COOH$. Such variants are denoted c1.

R' may selected from the group comprising or consisting of hydrogen, $C_1$-$C_6$ straight chain or branched alkyl, and $C_3$-$C_6$ cycloalkyl; and R may be selected from the group comprising or consisting of hydrogen; benzyl; $C_1$-$C_8$ straight chain and branched alkyl, alkenyl, and alkynyl; $C_3$-$C_6$ cycloalkyl; acyl groups $COR^1$ wherein $R^1$ is selected from the group comprising or consisting of $C_1$-$C_8$ straight chain and branched alkyl, alkenyl, and alkynyl, $C_3$-$C_6$ cycloalkyl, and phenyl; sulfamate esters ($SO_2NH_2$); acyl groups of naturally occurring amino acids; acyl groups of five-membered cyclic amino acid esters (amino group in 2 or 3 position); acyl groups of six-membered cyclic amino acid esters (amino group in 2, 3, or 4 position); $CONR^3R^4$ wherein $R^3$ and $R^4$ each independently is selected from $C_1$-$C_8$ straight chain and branched alkyl, alkenyl, and alkynyl and $C_3$-$C_6$ cycloalkyl; phosphate esters $PO_3^{2-}$ having counter ions selected from $Ca^{2+}$, $Na^+$, and $K^+$; phosphate esters $PO_3H^-$ having counter ions selected from $Ca^{2+}$, $Na^+$, and $K^+$; $CO(CH)_2COOH$; $CO(CH_2)_2COOH$; and $CO(CH_2)_3COOH$. Such variants are denoted c2.

R' may selected from the group comprising or consisting of hydrogen and $C_1$-$C_3$ straight chain or branched alkyl; and R may be selected from the group comprising or consisting of hydrogen; benzyl; $C_1$-$C_{16}$ straight chain and branched alkyl, alkenyl, and alkynyl; $C_3$-$C_6$ cycloalkyl; acyl groups $COR^1$ wherein $R^1$ is selected from the group comprising or consisting of $C_1$-$C_6$ straight chain and branched alkyl, alkenyl, and alkynyl, $C_3$-$C_6$ cycloalkyl, phenyl; and substituted phenyl wherein the phenyl ring is substituted in any one or more positions with 1-5 identical or different substituents selected from the group consisting of fluoro, chloro, bromo, iodo, cyano, nitro, and trifluoromethyl; sulfamate esters ($SO_2NH_2$); acyl groups of naturally occurring amino acids; acyl groups of five-membered cyclic amino acid esters (amino group in 2 or 3 position); acyl groups of six-membered cyclic amino acid esters (amino group in 2, 3, or 4 position); $CONR^3R^4$ wherein $R^3$ and $R^4$ each independently is selected from $C_1$-$C_6$ straight chain and branched alkyl, alkenyl, and alkynyl and $C_3$-$C_6$ cycloalkyl; phosphate esters $PO_3^{2-}$ having counter ions selected from $Ca^{2+}$, $Na^+$, and $K^+$; phosphate esters $PO_3H^-$ having counter ions selected from $Ca^{2+}$, $Na^+$, and $K^+$; $CO(CH)_2COOH$; $CO(CH_2)_2COOH$; and $CO(CH_2)_3COOH$. Such variants are denoted c3.

R' may be methyl or ethyl; and

R may be selected from the group comprising or consisting of hydrogen; $C_1$-$C_6$ straight chain and branched alkyl, alkenyl, and alkynyl; $C_3$-$C_6$ cycloalkyl; acyl groups $COR^1$ wherein $R^1$ is selected from the group comprising or consisting of $C_1$-$C_6$ straight chain and branched alkyl, alkenyl, and alkynyl, $C_3$-$C_6$ cycloalkyl, phenyl; and substituted phenyl wherein the phenyl ring is substituted in any one or more positions with 1-5 identical or different substituents selected from the group consisting of fluoro, chloro, bromo, iodo, cyano, nitro, trifluoromethyl, $C_1$-$C_6$ straight chain and branched alkoxy, $C_1$-$C_6$ sulfoxy, —S—$C_1$-$C_6$ alkyl, $C_1$-$C_6$ straight chain and branched alkyl, $C_2$-$C_6$ straight chain and branched alkenyl, $C_2$-$C_6$ straight chain and branched alkynyl, COO—$C_1$-$C_6$ alkyl, and CON($C_1$-$C_6$ alkyl)$_2$; sulfamate esters ($SO_2NH_2$); $CONR^3R^4$ wherein $R^3$ and $R^4$ each independently is selected from $C_1$-$C_6$ straight chain and branched alkyl, alkenyl, and alkynyl and $C_3$-$C_6$ cycloalkyl; $CO(CH)_2COOH$; $CO(CH_2)_2COOH$; and $CO(CH_2)_3COOH$. Such variants are denoted c4.

X may be oxygen or sulphur. Such variants are denoted d1.

X may be oxygen. Such variants are denoted d2.

X may be sulphur. Such variants are denoted d3.

It is to be understood that each selection of each possible X, R group, R' group, and Ar group disclosed herein is to be interpreted as being disclosed for use in any combination with one or more of each and every other election of possible X, R group, R' group and Ar group disclosed herein.

Thus, in some embodiments, the invention provides compound of formula I, or a pharmaceutically acceptable salt or solvate thereof, for use in a method for the treatment of IPF, wherein the selections of X, R, R', and Ar are as listed below:

ArI+c1+d1, ArI+c2+d1, ArI+c3+d1, ArI+c4+d1, ArI+c1+d2, ArI+c2+d2, ArI+c3+d2, ArI+c4+d2, ArI+c1+d3, ArI+c2+d3, ArI+c3+d3, ArI+c4+d3, ArII+c1+d1, ArII+c2+d1, ArII+c3+d1, ArII+c4+d1, ArII+c1+d2, ArII+c2+d2, ArII+c3+d2, ArII+c4+d2, ArII+c1+d3, ArII+c2+d3, ArII+c3+d3, ArII+c4+d3, ArIII+c1+d1, ArIII+c2+d1, ArIII+c3+d1, ArIII+c4+d1, ArIII+c1+d2, ArIII+c2+d2, ArIII+c3+d2, ArIII+c4+d2, ArIII+c1+d3, ArIII+c2+d3, ArIII+c3+d3, ArIII+c4+d3, ArIV+c1+d1, ArIV+c2+d1, ArIV+c3+d1, ArIV+c4+d1, ArIV+c1+d2, ArIV+c2+d2, ArIV+c3+d2, ArIV+c4+d2, ArIV+c1+d3, ArIV+c2+d3, ArIV+c3+d3, ArIV+c4+d3, ArV+c1+d1, ArV+c2+d1, ArV+c3+d1, ArV+c4+d1, ArV+c1+d2, ArV+c2+d2, ArV+c3+d2, ArV+c4+d2, ArV+c1+d3, ArV+c2+d3, ArV+c3+d3, ArV+c4+d3, ArVI+c1+d1, ArVI+c2+d1, ArVI+c3+d1, ArVI+c4+d1, ArVI+c1+d2, ArVI+c2+d2, ArVI+c3+d2, ArVI+c4+d2, ArVI+c1+d3, ArVI+c2+d3, ArVI+c3+d3, ArVI+c4+d3, ArVII+c1+d1, ArVII+c2+d1, ArVII+c3+d1, ArVII+c4+d1, ArVII+c1+d2, ArVII+c2+d2, ArVII+c3+d2, ArVII+c4+d2, ArVII+c1+d3, ArVII+c2+d3, ArVII+c3+d3, ArVII+c4+d3, ArVIII+c1+d1, ArVIII+c2+d1, ArVIII+c3+d1, ArVIII+c4+d1, ArVIII+c1+d2, ArVIII+c2+d2, ArVIII+c3+d2, ArVIII+c4+d2, ArVIII+c1+d3, ArVIII+c2+d3, ArVIII+c3+d3, ArVIII+c4+d3, ArIX+c1+d1, ArIX+c2+d1, ArIX+c3+d1, ArIX+c4+d1, ArIX+c1+d2, ArIX+c2+d2, ArIX+c3+d2, ArIX+c4+d2, ArIX+c1+d3, ArIX+c2+d3, ArIX+c3+d3, ArIX+c4+d3, ArX+c1+d1, ArX+c2+d1, ArX+c3+d1, ArX+c4+d1, ArX+c1+d2, ArX+c2+d2, ArX+c3+d2, ArX+c4+d2, ArX+c1+d3, ArX+c2+d3, ArX+c3+d3, ArX+c4+d3, ArXI+c1+d1, ArXI+c2+d1, ArXI+c3+d1, ArXI+c4+d1, ArXI+c1+d2, ArXI+c2+d2, ArXI+c3+d2, ArXI+c4+d2, ArXI+c1+d3, ArXI+c2+d3, ArXI+c3+d3, ArXI+c4+d3, ArXII+c1+d1, ArXII+c2+d1, ArXII+c3+d1, ArXII+c4+d1, ArXII+c1+d2, ArXII+c2+d2, ArXII+c3+d2, ArXII+c4+d2, ArXII+c1+d3, ArXII+c2+d3, ArXII+c3+d3, ArXII+c4+d3, ArXIII+c1+d1, ArXIII+c2+d1, ArXIII+c3+d1, ArXIII+c4+d1, ArXIII+c1+d2, ArXIII+c2+d2, ArXIII+c3+d2, ArXIII+c4+d2, ArXIII+c1+d3, ArXIII+c2+d3, ArXIII+c3+d3, ArXIII+c4+d3, ArXIV+c1+d1, ArXIV+c2+d1, ArXIV+c3+d1, ArXIV+c4+d1, ArXIV+c1+d2,

ArXIV+c2+d2, ArXIV+c3+d2, ArXIV+c4+d2, ArXIV+c1+d3, ArXIV+c2+d3, ArXIV+c3+d3, ArXIV+c4+d3, ArXV+c1+d1, ArXV+c2+d1, ArXV+c3+d1, ArXV+c4+d1, ArXV+c1+d2, ArXV+c2+d2, ArXV+c3+d2, ArXV+c4+d2, ArXV+c1+d3, ArXV+c2+d3, ArXV+c3+d3, ArXV+c4+d3, ArXVI+c1+d1, ArXVI+c2+d1, ArXVI+c3+d1, ArXVI+c4+d1, ArXVI+c1+d2, ArXVI+c2+d2, ArXVI+c3+d2, ArXVI+c4+d2, ArXVI+c1+d3, ArXVI+c2+d3, ArXVI+c3+d3, ArXVI+c4+d3, ArXVII+c1+d1, ArXVII+c2+d1, ArXVII+c3+d1, ArXVII+c4+d1, ArXVII+c1+d2, ArXVII+c2+d2, ArXVII+c3+d2, ArXVII+c4+d2, ArXVII+c1+d3, ArXVII+c2+d3, ArXVII+c3+d3, ArXVII+c4+d3, ArXVIII+c1+d1, ArXVIII+c2+d1, ArXVIII+c3+d1, ArXVIII+c4+d1, ArXVIII+c1+d2, ArXVIII+c2+d2, ArXVIII+c3+d2, ArXVIII+c4+d2, ArXVIII+c1+d3, ArXVIII+c2+d3, ArXVIII+c3+d3, ArXVIII+c4+d3, ArXIX+c1+d1, ArXIX+c2+d1, ArXIX+c3+d1, ArXIX+c4+d1, ArXIX+c1+d2, ArXIX+c2+d2, ArXIX+c3+d2, ArXIX+c4+d2, ArXIX+c1+d3, ArXIX+c2+d3, ArXIX+c3+d3, ArXIX+c4+d3, ArXX+c1+d1, ArXX+c2+d1, ArXX+c3+d1, ArXX+c4+d1, ArXX+c1+d2, ArXX+c2+d2, ArXX+c3+d2, ArXX+c4+d2, ArXX+c1+d3, ArXX+c2+d3, ArXX+c3+d3, ArXX+c4+d3, ArXX+c4+d2, ArXX+c1+d3, ArXX+c2+d3, ArXX+c3+d3, ArXX+c4+d3, ArXXI+c1+d1, ArXXI+c2+d1, ArXXI+c3+d1, ArXXI+c4+d1, ArXXI+c1+d2, ArXXI+c2+d2, ArXXI+c3+d2, ArXXI+c4+d2, ArXXI+c1+d3, ArXXI+c2+d3, ArXXI+c3+d3, ArXXI+c4+d3, ArXXII+c1+d1, ArXXII+c2+d1, ArXXII+c3+d1, ArXXII+c4+d1, ArXXII+c1+d2, ArXXII+c2+d2, ArXXII+c3+d2, ArXXII+c4+d2, ArXXII+c1+d3, ArXXII+c2+d3, ArXXII+c3+d3, ArXXII+c4+d3, ArXXIII+c1+d1, ArXXIII+c2+d1, ArXXIII+c3+d1, ArXXIII+c4+d1, ArXXIII+c1+d2, ArXXIII+c2+d2, ArXXIII+c3+d2, ArXXIII+c4+d2, ArXXIII+c1+d3, ArXXIII+c2+d3, ArXXIII+c3+d3, ArXXIII+c4+d3, ArXXIV+c1+d1, ArXXIV+c2+d1, ArXXIV+c3+d1, ArXXIV+c4+d1, ArXXIV+c1+d2, ArXXIV+c2+d2, ArXXIV+c3+d2, ArXXIV+c4+d2, ArXXIV+c1+d3, ArXXIV+c2+d3, ArXXIV+c3+d3, ArXXIV+c4+d3, ArXXV+c1+d1, ArXXV+c2+d1, ArXXV+c3+d1, ArXXV+c4+d1, ArXXV+c1+d2, ArXXV+c2+d2, ArXXV+c3+d2, ArXXV+c4+d2, ArXXV+c1+d3, ArXXV+c2+d3, ArXXV+c3+d3, ArXXV+c4+d3, ArXXVI+c1+d1, ArXXVI+c2+d1, ArXXVI+c3+d1, ArXXVI+c4+d1, ArXXVI+c1+d2, ArXXVI+c2+d2, ArXXVI+c3+d2, ArXXVI+c4+d2, ArXXVI+c1+d3, ArXXVI+c2+d3, ArXXVI+c3+d3, ArXXVI+c4+d3, ArXXVII+c1+d1, ArXXVII+c2+d1, ArXXVII+c3+d1, ArXXVII+c4+d1, ArXXVII+c1+d2, ArXXVII+c2+d2, ArXXVII+c3+d2, ArXXVII+c4+d2, ArXXVII+c1+d3, ArXXVII+c2+d3, ArXXVII+c3+d3, ArXXVII+c4+d3, ArXXVIII+c1+d1, ArXXVIII+c2+d1, ArXXVIII+c3+d1, ArXXVIII+c4+d1, ArXXVIII+c1+d2, ArXXVIII+c2+d2, ArXXVIII+c3+d2, ArXXVIII+c4+d2, ArXXVIII+c1+d3, ArXXVIII+c2+d3, ArXXVIII+c3+d3, ArXXVIII+c4+d3, ArXXIX+c1+d1, ArXXIX+c2+d1, ArXXIX+c3+d1, ArXXIX+c4+d1, ArXXIX+c1+d2, ArXXIX+c2+d2, ArXXIX+c3+d2, ArXXIX+c4+d2, ArXXIX+c1+d3, ArXXIX+c2+d3, ArXXIX+c3+d3, ArXXIX+c4+d3, ArXXX+c1+d1, ArXXX+c2+d1, ArXXX+c3+d1, ArXXX+c4+d1, ArXXX+c1+d2, ArXXX+c2+d2, ArXXX+c3+d2, ArXXX+c4+d2, ArXXX+c1+d3, ArXXX+c2+d3, ArXXX+c3+d3, ArXXX+c4+d3, ArXXXI+c1+d1, ArXXXI+c2+d1, ArXXXI+c3+d1, ArXXXI+c4+d1, ArXXXI+c1+d2, ArXXXI+c2+d2, ArXXXI+c3+d2, ArXXXI+c4+d2, ArXXXI+c1+d3, ArXXXI+c2+d3, ArXXXI+c3+d3, ArXXXI+c4+d3, ArXXXII+c1+d1, ArXXXII+c2+d1, ArXXXII+c3+d1, ArXXXII+c4+d1, ArXXXII+c1+d2, ArXXXII+c2+d2, ArXXXII+c3+d2, ArXXXII+c4+d2, ArXXXII+c1+d3, ArXXXII+c2+d3, ArXXXII+c3+d3, ArXXXII+c4+d3, ArXXXIII+c1+d1, ArXXXIII+c2+d1, ArXXXIII+c3+d1, ArXXXIII+c4+d1, ArXXXIII+c1+d2, ArXXXIII+c2+d2, ArXXXIII+c3+d2, ArXXXIII+c4+d2, ArXXXIII+c1+d3, ArXXXIII+c2+d3, ArXXXIII+c3+d3, ArXXXIII+c4+d3, ArXXXIV+c1+d1, ArXXXIV+c2+d1, ArXXXIV+c3+d1, ArXXXIV+c4+d1, ArXXXIV+c1+d2, ArXXXIV+c2+d2, ArXXXIV+c3+d2, ArXXXIV+c4+d2, ArXXXIV+c1+d3, ArXXXIV+c2+d3, ArXXXIV+c3+d3, ArXXXIV+c4+d3, ArXXXV+c1+d1, ArXXXV+c2+d1, ArXXXV+c3+d1, ArXXXV+c4+d1, ArXXXV+c1+d2, ArXXXV+c2+d2, ArXXXV+c3+d2, ArXXXV+c4+d2, ArXXXV+c1+d3, ArXXXV+c2+d3, ArXXXV+c3+d3, ArXXXV+c4+d3, ArXXXVI+c1+d1, ArXXXVI+c2+d1, ArXXXVI+c3+d1, ArXXXVI+c4+d1, ArXXXVI+c1+d2, ArXXXVI+c2+d2, ArXXXVI+c3+d2, ArXXXVI+c4+d2, ArXXXVI+c1+d3, ArXXXVI+c2+d3, ArXXXVI+c3+d3, ArXXXVI+c4+d3, ArXXXVII+c1+d1, ArXXXVII+c2+d1, ArXXXVII+c3+d1, ArXXXVII+c4+d1, ArXXXVII+c1+d2, ArXXXVII+c2+d2, ArXXXVII+c3+d2, ArXXXVII+c4+d2, ArXXXVII+c1+d3, ArXXXVII+c2+d3, ArXXXVII+c3+d3, ArXXXVII+c4+d3, ArXXXVIII+c1+d1, ArXXXVIII+c2+d1, ArXXXVIII+c3+d1, ArXXXVIII+c4+d1, ArXXXVIII+c1+d2, ArXXXVIII+c2+d2, ArXXXVIII+c3+d2, ArXXXVIII+c4+d2, ArXXXVIII+c1+d3, ArXXXVIII+c2+d3, ArXXXVIII+c3+d3, ArXXXVIII+c4+d3, ArXXXIX+c1+d1, ArXXXIX+c2+d1, ArXXXIX+c3+d1, ArXXXIX+c4+d1, ArXXXIX+c1+d2, ArXXXIX+c2+d2, ArXXXIX+c3+d2, ArXXXIX+c4+d2, ArXXXIX+c1+d3, ArXXXIX+c2+d3, ArXXXIX+c3+d3, ArXXXIX+c4+d3, ArXXXX+c1+d1, ArXXXX+c2+d1, ArXXXX+c3+d1, ArXXXX+c4+d1, ArXXXX+c1+d2, ArXXXX+c2+d2, ArXXXX+c3+d2, ArXXXX+c4+d2, ArXXXX+c1+d3, ArXXXX+c2+d3, ArXXXX+c3+d3, ArXXXX+c4+d3, ArXXXXI+c1+d1, ArXXXXI+c2+d1, ArXXXXI+c3+d1, ArXXXXI+c4+d1, ArXXXXI+c1+d2, ArXXXXI+c2+d2, ArXXXXI+c3+d2, ArXXXXI+c4+d2, ArXXXXI+c1+d3, ArXXXXI+c2+d3, ArXXXXI+c3+d3, ArXXXXI+c4+d3, ArXXXXII+c1+d1, ArXXXXII+c2+d1, ArXXXXII+c3+d1, ArXXXXII+c4+d1, ArXXXXII+c1+d2, ArXXXXII+c2+d2, ArXXXXII+c3+d2, ArXXXXII+c4+d2, ArXXXXII+c1+d3, ArXXXXII+c2+d3, ArXXXXII+c3+d3, ArXXXXII+c4+d3.

The letter-number combinations refer to the variants defined above, so that e.g. ArI+c1+d1 means that the aryl ring is an aryl ring without any heteroatoms (a1), that is substituted in from one to all positions with identical or different substituents selected from the group comprising or consisting of fluoro; chloro; bromo; iodo; cyano; nitro; trifluoromethyl; $C_1$-$C_6$ straight chain and branched alkoxy; $C_1$-$C_6$ sulfoxy; —S—$C_1$-$C_6$ alkyl; $C_1$-$C_{12}$ straight chain and branched alkyl, alkenyl, and alkynyl; $C_1$-$C_6$ fluoroalkyl, chloroalkyl, bromoalkyl, and iodoalkyl; COO—$C_1$-$C_6$ alkyl; N($C_1$-$C_6$ alkyl)$_2$; and CON($C_1$-$C_6$ alkyl)$_2$ (b1), R' is selected from the group comprising or consisting of hydrogen, $C_1$-$C_6$ straight chain or branched alkyl, and $C_3$-$C_6$ cycloalkyl; and R is selected from the group comprising or consisting of hydrogen; benzyl; $C_1$-$C_{18}$ straight chain and branched alkyl, alkenyl, and alkynyl; $C_3$-$C_6$ cycloalkyl; acyl groups $COR^1$ wherein $R^1$ is selected from the group comprising or consisting of $C_1$-$C_{18}$ straight chain and branched alkyl, alkenyl, and alkynyl, $C_3$-$C_6$ cycloalkyl, phenyl; and substituted phenyl wherein the phenyl ring is substituted in any one or more positions with 1-5 identical or different substituents selected from the group consisting of fluoro, chloro, bromo, iodo, cyano, nitro, trifluoromethyl, $C_1$-$C_6$ straight chain and branched alkoxy, $C_1$-$C_6$ sulfoxy, —S—$C_1$-$C_6$ alkyl, $C_1$-$C_6$ straight chain and branched alkyl, $C_2$-$C_6$ straight chain and branched alkenyl, $C_2$-$C_6$ straight chain and branched alkynyl, $C_1$-$C_6$ fluoroalkyl, chloroalkyl, bromoalkyl, and iodoalkyl, COO—$C_1$-$C_6$ alkyl, and CON($C_1$-$C_6$ alkyl)$_2$; sulfamate esters ($SO_2NH_2$); acyl groups of naturally occurring amino acids; acyl groups of five-membered cyclic amino acid esters (amino group in 2 or 3 position); acyl groups of six-membered cyclic amino acid esters (amino group in 2, 3, or 4 position); $CONR^3R^4$ wherein $R^3$ and $R^4$ each independently is selected from $C_1$-$C_{18}$ straight chain and branched alkyl, alkenyl, and alkynyl and $C_3$-$C_6$ cycloalkyl; phosphate esters $PO_3^{2-}$ having counter ions selected from $Ca^{2+}$, $Na^+$, and $K^+$; phosphate esters $PO_3H^-$ having counter ions selected from $Ca^{2+}$, $Na^+$, and $K^+$; $CO(CH)_2COOH$; $CO(CH_2)_2COOH$; and $CO(CH_2)_3COOH$ (c1), and that X is O or S—and so on for the other combinations.

For each of the listed combinations the α-β bond may be a single bond. For each of the listed combinations the α-@ bond may be a double bond. For each of the listed combinations the α-β bond is preferably a triple bond.

In some embodiments, the invention provides a compound of formula I, or a pharmaceutically acceptable salt or solvate thereof, for use in the treatment of IPF, wherein the selections of Ar, X, R, R', and the type of α-β bond, are as listed below:

Ar: Unsubstituted phenyl or naphthyl, optionally containing one or more heteroatoms selected from N, O, and/or S.

X: O or S.

R': Hydrogen, $C_1$-$C_6$ straight chain or branched alkyl, or $C_3$-$C_6$ cycloalkyl.

R: Acyl group $COR^1$ wherein $R^1$ is selected from the group comprising or consisting of $C_1$-$C_{18}$ straight chain and branched alkyl, alkenyl, and alkynyl, $C_3$-$C_6$ cycloalkyl, phenyl; and substituted phenyl wherein the phenyl ring is substituted in any one or more positions with 1-5 identical or different substituents selected from the group consisting of fluoro, chloro, bromo, iodo, cyano, nitro, trifluoromethyl, $C_1$-$C_6$ straight chain and branched alkoxy, $C_1$-$C_6$ sulfoxy, —S—$C_1$-$C_6$ alkyl, $C_1$-$C_6$ straight chain and branched alkyl, $C_2$-$C_6$ straight chain and branched alkenyl, $C_2$-$C_6$ straight chain and branched alkynyl, $C_1$-$C_6$ fluoroalkyl, chloroalkyl, bromoalkyl, and iodoalkyl, COO—$C_1$-$C_6$ alkyl, and CON($C_1$-$C_6$ alkyl)$_2$.

α-β bond: Single, double, or triple bond.

In some embodiments, the invention provides a compound of formula I, or a pharmaceutically acceptable salt or solvate thereof, for use in the treatment of IPF, wherein the selections of Ar, X, R, R', and the type of α-β bond, are as listed below:

Ar: Phenyl or naphthyl, substituted in any one or more positions with one or more identical or different substituents selected from the group comprising or consisting of fluoro; chloro; bromo; cyano, nitro, trifluoromethyl, COO—$C_1$-$C_6$ alkyl, and $C_1$-$C_6$ fluoroalkyl, chloroalkyl, bromoalkyl.

X: O or S.

R': Hydrogen or $C_1$-$C_4$ straight chain or branched alkyl.

R: Acyl group $COR^1$ wherein $R^1$ is selected from the group comprising or consisting of $C_1$-$C_8$ straight chain and branched alkyl, alkenyl, and alkynyl, $C_3$-$C_6$ cycloalkyl, and phenyl.

α-β bond: Triple bond.

In some embodiments, the invention provides a compound of formula I, or a pharmaceutically acceptable salt or solvate thereof, for use in the treatment of IPF, wherein the selections of Ar, X, R, R', and the type of α-β bond, are as listed below:

Ar: Phenyl or naphthyl, substituted in any one or more positions with one or more identical or different substituents selected from the group comprising or consisting of iodo, $C_1$-$C_6$ straight chain and branched alkoxy, $C_1$-$C_6$ sulfoxy, —S—$C_1$-$C_6$ alkyl, $C_1$-$C_6$ straight chain and branched alkyl, $C_2$-$C_6$ straight chain and branched alkenyl, $C_2$-$C_6$ straight chain and branched alkynyl, $C_1$-$C_6$ iodoalkyl, N($C_1$-$C_6$ alkyl)$_2$ and CON($C_1$-$C_6$ alkyl)$_2$.

X: O or S.

R': $C_1$-$C_6$ straight chain or branched alkyl.

R: Acyl group $COR^1$ wherein $R^1$ is selected from the group comprising or consisting of $C_1$-$C_6$ straight chain and branched alkyl, alkenyl, and alkynyl, $C_3$-$C_6$ cycloalkyl, phenyl; and substituted phenyl wherein the phenyl ring is substituted in any one or more positions with 1-5 identical or different substituents selected from the group consisting of fluoro, chloro, bromo, iodo, cyano, nitro, trifluoromethyl, $C_1$-C3 straight chain and branched alkoxy, $C_1$-$C_3$ sulfoxy, —S—$C_1$-$C_3$ alkyl, $C_1$-$C_3$ straight chain and branched alkyl, $C_2$-$C_3$ straight chain and branched alkenyl, $C_2$-$C_3$ straight chain and branched alkynyl, $C_1$-$C_3$ fluoroalkyl, chloroalkyl, bromoalkyl, and iodoalkyl, COO—$C_1$-C3 alkyl, and CON($C_1$-$C_3$ alkyl)$_2$.

α-β bond: Triple bond.

In some embodiments, the invention provides a compound of formula I, or a pharmaceutically acceptable salt or solvate thereof, for use in the treatment of IPF, wherein the selections of Ar, X, R, R', and the type of α-β bond, are as listed below:

Ar: Aryl group optionally containing one or more nitrogen, oxygen, or sulphur atoms, and optionally substituted in any one or more positions with one or more identical or different substituents selected from the group comprising or consisting of fluoro; chloro; bromo; iodo, cyano, nitro, trifluoromethyl, $C_1$-$C_8$ straight chain and branched alkoxy, $C_1$-$C_6$ sulfoxy, —S—$C_1$-$C_6$ alkyl, $C_1$-$C_6$ straight chain and branched alkyl, $C_2$-$C_6$ straight chain and branched alkenyl, $C_2$-$C_6$ straight chain and branched alkynyl, $C_1$-$C_6$ fluoroalkyl, chloroalkyl, bromoalkyl, and iodoalkyl, COO—$C_1$-$C_6$ alkyl, N($C_1$-$C_6$ alkyl)$_2$ and CON($C_1$-$C_5$ alkyl)$_2$, and more preferably the aryl group is optionally substituted with one or more identical or different substituents selected from the group of nitro, trifluoromethyl, $C_1$-$C_6$ straight chain and branched alkoxy, $C_1$-$C_6$ straight chain and branched alkyl.

X: O or S.

R': Hydrogen, $C_1$-$C_6$ straight chain or branched alkyl, or $C_3$-$C_6$ cycloalkyl, and more preferably hydrogen, $C_1$-$C_6$ straight chain or branched alkyl.

R: hydrogen; $C_1$-$C_6$ straight chain or branched alkyl, alkenyl, or alkynyl; $C_3$-$C_6$ cycloalkyl; acyl groups $COR^1$ wherein $R^1$ is selected from the group comprising or consisting of $C_1$-$C_6$ straight chain and branched alkyl, alkenyl, and alkynyl, $C_3$-$C_6$ cycloalkyl and phenyl, and more preferably H or acetyl.

α-β bond: Double or triple bond, and more preferably a triple bond.

Non-limiting examples of compounds according to the invention for use in a method for the treatment of IPF include:

N-[(4-Hydroxy-3-methoxyphenyl)methyl]-7-phenyl-6-heptynamide; (2)

2-Methoxy-4-[(6-phenyl-5-hexynylcarbonylamino)methyl] phenyl acetate (5);

N-[(4-Hydroxy-3-methoxyphenyl)methyl]-(E)-7-phenyl-6-heptenamide;

N-[(4-Hydroxy-3-methoxyphenyl)methyl]7-phenylheptanamide (8);

N-[(4-Hydroxy-3-methoxyphenyl)methyl]-7-(p-methoxyphenyl)-6-heptynamide (11);

N-[(4-Hydroxy-3-methoxyphenyl)methyl]-7-(p-nitrophenyl)-6-heptynamide (10);

N-[(4-Hydroxy-3-methoxyphenyl)methyl]-7-(1-naphthyl)-6-heptynamide (12);

N-{[4-(Benzyloxy)-3-methoxyphenyl]methyl}-7-(p-methoxyphenyl)-6-heptynamide;

3-{2-Methoxy-4-[(6-phenyl-5-hexynylcarbonylamino) methyl]phenoxycarbonyl} propionic acid;

2-Methoxy-4-[(6-phenyl-5-hexynylcarbonylamino)methyl] phenyl hexadecanoate.

In some embodiments, the invention provides a compound of formula I, or a pharmaceutically acceptable salt or solvate thereof, for use in the treatment of IPF, wherein the compound is selected from the group of phenyl-substituted 6-yne derivatives of capsaicin, often referred to as phenylcapsaicins, wherein Ar is unsubstituted phenyl or substituted phenyl as defined above (variants ArXV-ArXXI), R' is selected from hydrogen, $C_1$-$C_6$ straight chain or branched alkyl, and R is H or a $C_1$-$C_6$ straight chain or branched alkyl, alkenyl, and alkynyl; $C_3$-$C_6$ cycloalkyl; acyl groups $COR^1$ wherein $R^1$ is selected from the group comprising or consisting of $C_1$-$C_6$ straight chain and branched alkyl, alkenyl, and alkynyl, $C_3$-$C_6$ cycloalkyl and phenyl, and more preferably R is H or an acyl group.

In some embodiments, the invention provides a compound of formula I, as disclosed above, wherein the α-β bond is a triple bond as shown in formula II, or a pharmaceutically acceptable salt or solvate thereof, for use in the treatment of IPF. The Ar group is unsubstituted phenyl or substituted phenyl as defined above (variants ArXV-ArXXI). The R' and R groups are as defined above, and more preferably R' is H, or $C_1$-$C_6$ straight chain or branched alkyl, R is H or a $C_1$-$C_5$ straight chain or branched acyl group, and X is S or O.

II

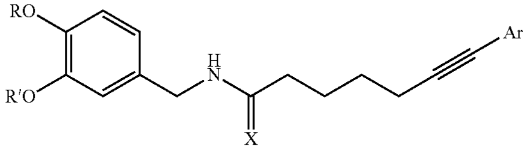

In some embodiments, the invention provides a compound of formula II, or a pharmaceutically acceptable salt or solvate thereof, for use in the treatment of IPF, wherein Ar is unsubstituted phenyl or substituted phenyl as defined above (variants ArXV-ArXXI), R' is $C_1$-$C_3$ straight chain or branched alkyl, R is H or a $C_1$-$C_5$ straight chain or branched acyl group, and X is O.

In some embodiments, the invention provides a compound of formula II, or a pharmaceutically acceptable salt or solvate thereof, for use in the treatment of IPF, wherein Ar is a substituted phenyl, substituted with at least one alkoxy group, R' is a $C_1$-$C_3$ straight chain or branched alkyl, R is H or a $C_1$-$C_5$ straight chain or branched acyl group, and X is O.

In some embodiments, the invention provides a compound of formula III, or a pharmaceutically acceptable salt or solvate thereof, for use in the treatment of IPF, wherein Ph denotes unsubstituted phenyl, R' is $C_1$-$C_3$ straight chain or branched alkyl, R is H or a $C_1$-$C_5$ straight chain or branched acyl group, and X is S or O.

III

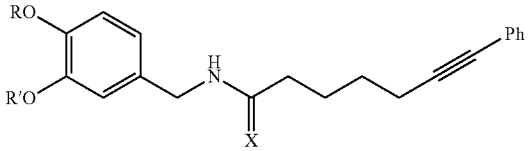

In some embodiments, the invention provides a compound of formula III, or a pharmaceutically acceptable salt or solvate thereof, for use in the treatment of IPF, wherein Ph denotes unsubstituted phenyl, R' is $C_1$-$C_3$ straight chain or branched alkyl, R is H or a $C_1$-$C_5$ straight chain or branched acyl group, and X is O.

In some embodiments, the invention provides a compound of formula III, or a pharmaceutically acceptable salt or solvate thereof, for use in the treatment of IPF, wherein Ph denotes unsubstituted phenyl, R' is methyl, R is H or $C_1$-$C_5$ straight chain or branched acyl, and X is O. In one embodiment R' is methyl and R is acetyl.

In some embodiments, the invention provides a compound of formula III, or a pharmaceutically acceptable salt or solvate thereof, for use in the treatment of IPF, wherein Ph denotes unsubstituted phenyl, R' is methyl, R is H or acetyl, and X is O.

The compounds of the invention may contain one or more chiral centres and/or double bonds, and may therefore exist in different stereoisomeric forms, such as double-bond isomers (i.e., geometric isomers), enantiomers, and/or diastereomers. It is to be understood that both stereomerically pure forms (e.g., geometrically pure, enantiomerically pure, or diastereomerically pure) and stereoisomeric mixtures are encompassed in the invention. The invention is considered to extend to diastereomers and enantiomers, as well as racemic mixtures.

Compounds herein described may be resolved into their geometric isomers, enantiomers and/or diastereomers, using methods known in the art.

The compounds may be obtained commercially or using any procedure known to the person skilled in the art. Non-limiting examples of procedures for obtaining the compounds according to the invention are those disclosed by the applicant in EP 1670310 and in the Norwegian patent application NO 20200333.

Former and current smokers are more likely to develop IPF than those who have never smoked. A family history of IPF is also a risk factor—around 1 in 20 IPF patients has a family member with the disease—as are certain genes. IPF has also been linked to gastroesophageal reflux, certain viral infections, air pollution, and exposure to certain types of dust, such as metal or wood dust. It is not known whether any of these factors directly cause IPF. People in their 60s and 70s are most commonly affected, and the disease is rare in people under 50. Males are affected more often than females. One study estimated that idiopathic pulmonary fibrosis affects 1 out of 200 adults over the age of 70 in the United States.

IPF has also been recognized in several breeds of both dogs and cats. Veterinary patients with the condition share many of the same symptoms as their human counterparts, including increased respiratory rate and eventual respiratory distress, and also have a generally poor prognosis.

The patient group of the present invention comprises patients diagnosed with or suspected of having an ILD, preferably an idiopathic ILD and/or a pulmonary fibrosis, more preferably IPF. The patient group may consist of patients suffering from IPF, such as patients diagnosed with or suspected of having IPF. In preferred embodiments, a subject is selected from this patient group. The subject may be a human or a non-human animal, such as a human or non-human mammal, preferably a human patient. The subject may be male or female. In some embodiments, the subject is an adult (i.e. 18 years of age or older). In certain embodiments, the subject is geriatric. In certain embodiments, the subject is not geriatric. In some embodiments, the subject is a human over 50 years of age, such as over 60 years of age, such as over 70 years of age.

As used herein, “subject” means any human or non-human animal selected for treatment or therapy, and encompasses, and may be limited to, “patient”. None of the terms should be construed as requiring the supervision (constant or otherwise) of a medical professional (e.g., physician, nurse, nurse practitioner, physician’s assistant, orderly, clinical research associate, etc.) or a scientific researcher.

Any of the compounds according to the invention may be provided in the form of a prodrug. As used herein, the term “prodrug” means any compound which under physiological conditions is converted into any of the compounds according to the invention. A prodrug may, but need not necessarily, be pharmacologically inactive until converted into the active compound. A prodrug may be obtained by derivatising one or more functional groups in the active compound with a progroup, i.e. a group that masks a functional group within the active compound and that undergoes a transformation under the specified conditions of use, such as in vivo, to release said functional group. The progroup should be nontoxic. A wide range of progroups, and methods for providing prodrugs, are known to the person skilled in the art.

The compounds for use in the treatment of IPF may according to the invention be present as an active ingredient in a desired dosage unit formulation, such as a pharmaceutically acceptable composition containing one or more conventional pharmaceutically acceptable carriers. As used herein, the term “composition” refers to a mixture, in any formulation, of one or more compounds according to the invention with one or more additional chemical component.

Hence, in another aspect, the invention provides a composition for use in a method the treatment of IPF.

Compositions for use in a method for the treatment of IPF according to the invention are prepared from the compounds disclosed herein in substantially pure form. In some embodiments, the purity of the compound according to the invention used to formulate the composition is at least about 95%, such as at least 96%, 97%, 98%, or 99%. Preferably, the purity of the compound is at least 98%.

The composition may further include one or more of any conventional, pharmaceutically acceptable excipients and/or carriers, e.g. solvents, fillers, diluents, binders, lubricants, glidants, viscosity modifiers, surfactants, dispersing agents, disintegration agents, emulsifying agents, wetting agents, suspending agents, thickeners, buffers, pH modifiers, absorption-delaying agents, stabilisers, antioxidants, preservatives, antimicrobial agents, antibacterial agents, antifungal agents, chelating agents, adjuvants, sweeteners, aromas, and colouring agents. Conventional formulation techniques known in the art, e.g., conventional mixing, dissolving, suspending, granulating, drageemaking, levigating, emulsifying, encapsulating, entrapping or compressing processes, may be used to formulate the composition.

In some embodiments, the composition for use in a method for the treatment of IPF is formulated for pulmonal, oral, and/or intravenous administration. In some embodiments the composition is formulated for inhalation, such as in the form of an aerosol inhalation formulation.

The amount of the compound according to the invention present in the composition can vary. In some embodiments, the amount of the compound according to the invention present in the composition is 1-50% by weight, such as 1-30%, such as 20-50%. In other embodiments, the amount of the compound according to the invention present in the composition is 30-70% by weight, such as 40-60%. In yet other embodiments, the amount of the compounds according to the invention present in the composition is 50-100% by weight, such as 50-70%, such as 50-80%, such as 60-98%, such as 70-95%, such as 80-99%, such as 95-100%.

Further, the composition for use in a method for the treatment of IPF according to the invention is substantially free of contaminants or impurities. In some embodiments, the level of contaminants or impurities other than residual solvent in the composition is below about 5% relative to the combined weight of the compounds according to the invention and the intended other ingredients. In certain embodiments, the level of contaminants or impurities other than residual solvent in the composition is no more than about 2% or 1% relative to the combined weight of the compounds according to the invention and the intended other ingredients.

Advantageously, the compound or composition for use in a method for the treatment of IPF according to the invention is sterile. Sterilisation can be achieved by any suitable method, including but not limited to by applying heat, chemicals, irradiation, high pressure, filtration, or combinations thereof.

The compound or composition for use in a method for the treatment of IPF will according to the invention be administered to a subject in a therapeutically effective dose. As used herein, the term “therapeutically effective dose” means the amount of compound according to the invention which is effective for producing the desired therapeutic effect in a subject at a reasonable benefit/risk ratio applicable to any treatment. The therapeutically effective dosage amount may vary depending upon the route of administration and dosage form. Appropriate dosages may depend on the compound to be used, the stage of the condition, age and weight of the patient, etc. and may be routinely determined by the skilled practitioner according to principles well known in the art. A suitable daily dosage of the compound according to the invention may range from about 0.01 mg/kg body weight to 1.0 mg/kg body weight. For example, in some embodiments, the daily dose may be 0.01-0.1 mg/kg body weight, such as 0.01-0.05 mg/kg body weight such as 0.03-0.08 mg/kg body weight, such as 0.05-0.1 mg/kg body weight. In other embodiments, the daily dose may be 0.05-0.5 mg/kg body weight, such as 0.05-0.02 mg/kg body weight, such as 0.08-0.5 mg/kg body weight. In yet other embodiments, the daily dose may be 0.1-1.0 mg/kg body weight, such as 0.3-0.08 mg/kg body weight, such as 0.5-1.0 mg/kg body weight.

The therapeutically effective dose can be administered in a single dose or in divided doses. The compound or composition according to the invention can be administered once, twice or more times a day, once every two days, once every three days, twice a week or once a week, or as deemed appropriate by a medical professional. In certain embodiments, the compound or composition according to the invention is administered once daily. In other embodiments, the compound or composition according to the invention is administered twice daily. In some embodiments, the dosage regimen is predetermined and the same for the entire patient group. In other embodiments, the dosage and the frequency of administration of treatment with the compound or composition according to the invention is determined by a medical professional, based on factors including, but not limited to, the stage of the disease, the severity of symptoms, the route of administration, the age, body weight, general health, gender and/or diet of the subject, and/or the response of the subject to the treatment.

In some embodiments, the therapeutically effective dose is administered at regular intervals. In other embodiments, the dose is administered when needed or sporadically. The compound or composition according to the invention may be administered by a medical professional or by self-administration. The compound or composition according to the invention may, depending on factors such as formulation and route of administration, be administered with food or without food. In some embodiments, the compound or composition according to the invention is administered at specific times of day.

As used herein, the terms "administer", "administration", and "administering" refer to (1) providing, giving, dosing and/or prescribing by either a health practitioner or their authorised agent or under their direction, or by self-administration, a formulation, preparation or composition according to the present disclosure, and (2) putting into, taking or consuming by the subject themselves, a formulation, preparation or composition according to the present disclosure.

The compound or composition for use in a method for the treatment of IPF according to the invention may be administered locally or systemically. The compound or composition according to the invention may be administered by any administration route, including but not limited to, pulmonary, orally, intravenously, intramuscularly, sublingually, subcutaneously, buccally, nasally, and transdermally.

In preferred embodiments, the compound or composition is administered pulmonary, orally, and/or intravenously.

In some embodiments, the compound or composition for use in a method for the treatment of IPF according to the invention is administered via a pulmonary route, e.g. by inhalation or insufflation of powders or aerosols, including by nebulizer, intratracheal, intranasal, epidermal and transdermal). In specific embodiments, the compound or composition is administered by inhalation by oral, nasal, or bronchial routes, such as via aerosol inhalation, such as spray inhalation, such as using, for example, inhalers known in the art. In specific embodiments, the compound or composition according to the invention is in the form of aerosol particles, either solid or liquid, preferably of respirable size. Such particles are sufficiently small to pass through the mouth and larynx upon inhalation and into the bronchi and alveoli of the lungs. In general, particles ranging from about 1 to 10 microns in size, and preferably less than about 5 microns in size, are respirable.

In some embodiments, the compound or composition is administered orally. In some embodiments, the compound or composition is administered with a meal or before a meal.

In some embodiments, the compound or composition according to the invention is administered intravenously. In these embodiments, water is a particularly useful excipient. Saline solutions and aqueous dextrose and glycerol solutions can also be employed as liquid excipients, particularly for injectable solutions.

Preferred unit dosage formulations are those containing a therapeutically effective dose, as hereinbefore recited, or an appropriate fraction thereof, of a compound for use in a method for the treatment of IPF according to the invention. A composition for use in a method for the treatment of IPF may be presented in unit dosage form as a single dose wherein all active and inactive ingredients are combined in a suitable system and components do not need to be mixed before administration. Alternatively, a composition may be presented as a kit in which the drug, excipients and carriers are provided in two or more separate containers (e.g., ampules, vials, tubes, bottles or syringes) and need to be combined to form the composition to be administered. A kit may contain one or more compounds according to the invention or a composition according to the invention and all other ingredients in unit dosage form, or in two or more separate containers, and may contain instructions for storing, preparing, administering and/or using the composition.

In some embodiments, the duration of the use of the compound or composition for use in a method for the treatment of IPF according to the invention is determined by clinical, physiological, and/or imaging information, such as pulmonary function tests. In some embodiments, treatment is sustained until no further improvement can be expected based on clinical, physiological, and/or imaging information, such as pulmonary function tests. In certain embodiments, the duration of the treatment with the compound or composition according to the invention is at least two weeks, at least one month, at least three months, such as three months, six months, nine months, a year, three years, five years. In other embodiments, the duration is determined by a medical professional, based on factors including but not limited to the nature and severity of the symptoms, the route of administration, the age, body weight, general health, gender and/or diet of the subject, and/or the response of the subject to the treatment. In other embodiments, the compound or composition is administered chronically, such as in a continuous mode as opposed to an acute mode, so as to maintain the initial therapeutic effect for an extended period of time.

In certain embodiments, the compound or composition according to the invention is administered alone. In other embodiments, the compound or composition according to the invention is administered in combination with one or more other therapeutic agents. Said one or more other therapeutic agents may be known to have an effect against IPF and/or may have an additive or synergistic mechanism of action on IPF treatment together with the compound or composition of the invention. In some embodiments, the compound or composition according to the invention is administered as part of a combination therapy.

Combination therapies comprising a compound or composition according to the invention may refer to compositions that comprise the compound or composition according to the invention in combination with one or more therapeutic agents, and/or co-administration of the compound or composition according to the invention with one or more therapeutic agents wherein the compound or composition according to the invention and the other therapeutic agent or agents have not been formulated in the same composition. When using separate formulations, the compound or composition according to the invention may be administered simultaneously, intermittent, staggered, prior to, subsequent to, or combinations of these, with the administration of another therapeutic agent.

In a further aspect, the invention provides a kit comprising i) a compound of formula I, or any pharmaceutically acceptable salt or solvate thereof; and ii) an inhaler.

In a further aspect, the invention provides a kit comprising i) a composition comprising a compound of formula I, or any pharmaceutically acceptable salt or solvate thereof, formulated for inhalation; and ii) an inhaler.

As used herein, the term inhaler encompasses all types of devices suitable for nasal and/or pulmonary administration of a compound or composition, such as into any part of the lungs of a subject, including but not limited to mechanical metered dose inhalers (MDIs) such as pressurised MDIs, breath-actuated MDIs, dry powder inhalers, inhalers with spacer devices, and nebulisers.

The embodiments and features described in the context of one aspect, e.g. for the aspect directed to the compound for use in a method for the treatment of IPF, also apply to the other aspects of the invention, such as the composition for use in a method for the treatment of IPF, such as the kit, such as the method of treatment of IPF.

In a further aspect, the invention provides a method of treatment of idiopathic pulmonary fibrosis, the method comprising the step of administering an effective amount of a compound of formula I, or any pharmaceutically acceptable salt or solvate thereof, to a subject in need thereof.

In some embodiments, the invention provides a method of treatment of idiopathic pulmonary fibrosis, the method comprising the step of administering a composition comprising an effective amount of a compound of formula I, or any pharmaceutically acceptable salt or solvate thereof, to a subject in need thereof.

In a further aspect, the invention provides a method of treatment of idiopathic pulmonary fibrosis, the method comprising the step of administering to the subject an effective amount of phenylcapsaicin, or any pharmaceutically acceptable salt or solvate thereof, to a subject in need thereof.

In some embodiments, the invention provides a method of treatment of idiopathic pulmonary fibrosis, the method comprising the step of administering to the subject a composition comprising an effective amount of phenylcapsaicin, or any pharmaceutically acceptable salt or solvate thereof to a subject in need thereof.

In a yet a further aspect, the invention provides a method for inhibiting the activity of platelet-derived growth factor receptor (PDGF)-α and/or β in a subject in need thereof, the method comprising the step of administering an effective amount of a compound of formula I, or any pharmaceutically acceptable salt or solvate thereof, to the subject.

The invention shall not be limited to the shown embodiments and examples. While various embodiments of the present disclosure are described herein, it will be obvious to those skilled in the art that such embodiments are provided by way of example only. Numerous modifications and changes to, and variations and substitutions of, the embodiments described herein will be apparent to those skilled in the art without departing from the disclosure. It is to be understood that various alternatives to the embodiments described herein can be employed in practicing the disclosure.

It is to be understood that every embodiment of the disclosure can optionally be combined with any one or more of the other embodiments described herein.

It is to be understood that each component, compound, or parameter disclosed herein is to be interpreted as being disclosed for use alone or in combination with one or more of each and every other component, compound, or parameter disclosed herein. It is further to be understood that each amount/value or range of amounts/values for each component, compound, or parameter disclosed herein is to be interpreted as also being disclosed in combination with each amount/value or range of amounts/values disclosed for any other component(s), compound(s), or parameter(s) disclosed herein, and that any combination of amounts/values or ranges of amounts/values for two or more component(s), compound(s), or parameter(s) disclosed herein are thus also disclosed in combination with each other for the purposes of this description. Any and all features described herein, and combinations of such features, are included within the scope of the present invention provided that the features are not mutually inconsistent.

It is to be understood that each lower limit of each range disclosed herein is to be interpreted as disclosed in combination with each upper limit of each range disclosed herein for the same component, compound, or parameter. Thus, a disclosure of two ranges is to be interpreted as a disclosure of four ranges derived by combining each lower limit of each range with each upper limit of each range. A disclosure of three ranges is to be interpreted as a disclosure of nine ranges derived by combining each lower limit of each range with each upper limit of each range, etc. Furthermore, specific amounts/values of a component, compound, or parameter disclosed in the description or an example is to be interpreted as a disclosure of either a lower or an upper limit of a range and thus can be combined with any other lower or upper limit or a range or specific amount/value for the same component, compound, or parameter disclosed elsewhere in the application to form a range for that component, compound, or parameter.

EXAMPLES

Example 1—Reduction of PDGF-Supported Survival and Proliferation of Human Corneal Epithelial Cells in the Presence of Phenylcapsaicin An assay was performed in order to study the mediation of PDGF-supported survival and proliferation of human corneal epithelial cells in the presence of increasing concentrations of phenylcapsaicin.

Method:

Cell Culture:

Primary isolated human corneal epithelial cells; Normal, Human cells (ATCC® PCS-700-010™) were maintained in culture at 37° C. with 5% $CO_2$ and 95% humidity in serum reduced (5% fetal calf serum) modified promocell media (MPM) supplemented with 4 ng/ml fibronectin (FN), 2 ng/ml human recombinant vascular endothelial growth factor (VEGF) and 4 ng/ml basic fibroblast growth factor (bFGF). This combination of FN, VEGF and bFGF has been shown to optimize growth and migration kinetics.

Clonogenic Cell Survival Assay:

A clonogenic cell survival assay determines the ability of a cell to proliferate indefinitely. The effects of phenylcapsaicin (2) on clonogenic survival of corneal epithelial cells was investigated by plating the cells with increasing numbers (102 to 5×104) in 25 $cm^2$ flasks. SU9518, a known inhibitor PDGF that has shown the ability to reduce radiation-induced fibroblast and endothelial cell activation, was used as the positive control. The cells were incubated with 0-10 μM of phenylcapsaicin and SU9518 separately in the presence of 10 ng/ml PDGF-AB. The flasks were returned to the incubator for 14 days, after which they were stained with crystal violet. The colonies were counted, and the surviving Proliferation Assay:

Corneal cells were harvested by trypsinization at 37° C. and neutralized with trypsin-neutralizing solution. A suspension of 50,000 cells in MPM/DMEM was added to 25 ml flasks. The cells were incubated with phenylcapsaicin or SU9518 for 1 hour in cytokine-free medium at standard conditions and incubated for another 72 hours in the presence of final mediums (either with 10 ng/ml PDGF-AB+4 ng/ml FN, or with 2 ng/ml VEGF+4 ng/ml bFGF+4 ng/ml FN). The cells were then dispersed in trypsin, resuspended, and counted in a coulter counter.

Results:

Clonogenic Survival Assay Results:

The results from the clonogenic survival assay are shown in FIG. 1. In the clonogenic survival assay, the inhibitory effects of phenylcapsaicin exhibited a dose-dependant inhibitory effect on survival of human corneal epithelial cells in the presence of PDGF (-AB isoform, 10 ng/ml). SU9518, a known inhibitor of PDGF signalling which was used as a control, also showed a dose dependent reduction in cell survival.

Figure 2:
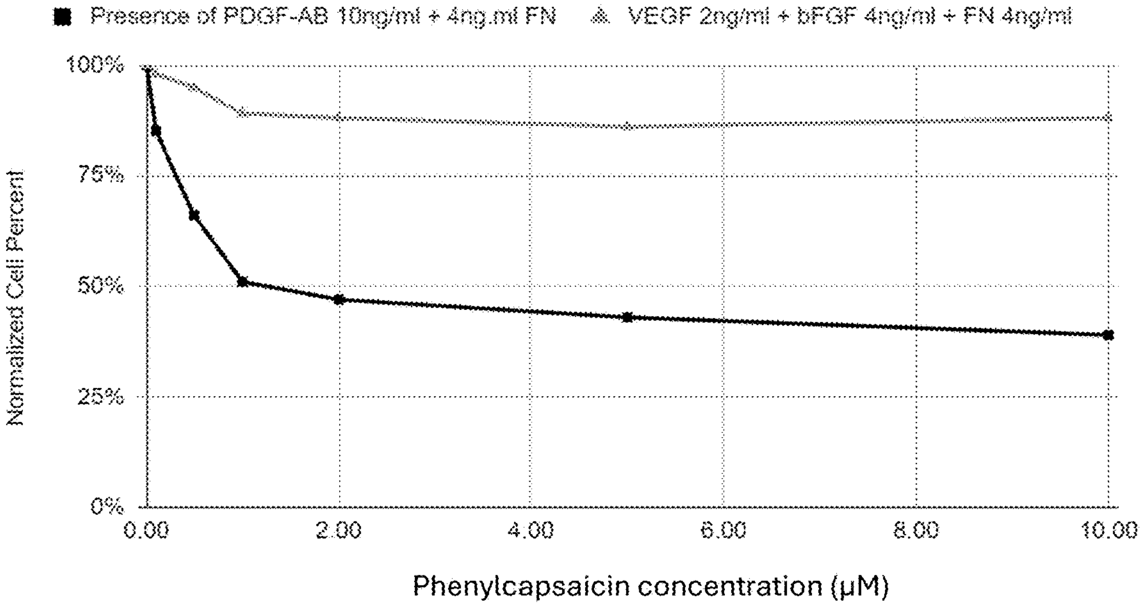
FIG. 2 shows the results from a proliferation assay studying PDGF-stimulated corneal epithelial proliferation.

Proliferation Assay Results:

To further evaluate the specificity of phenylcapsaicin, its ability to inhibit PDGF-stimulated corneal epithelial proliferation was compared to its inhibitory potency to epithelial proliferation stimulated by VEGF+bFGF was measured. As shown in FIG. 2, phenylcapsaicin inhibited 10 ng/ml PDGF-induced epithelial proliferation with an IC50 of ~1 μM whereas VEGF+bFGF-induced proliferation did not show an IC50 value up to the highest dose (10 uM) of phenylcapsaicin tested.

Discussion/Conclusion:

PDGF inhibition is considered a viable mechanistic pathway for the treatment of fibrosis and particularly pulmonary fibrosis. Inhibition of PDGF signalling in human corneal epithelial cells in the presence of phenylcapsaicin showed a reduction in the survival fraction of endothelial cells in a dose dependent manner. For example, at a 5 μM concentration, phenylcapsaicin reduced the surviving fraction of epithelial cells to 27% versus 30% for the positive control SU9518. Thus, it can be concluded that PDGF-mediated clonogenic survival of human corneal epithelial cells is significantly inhibited by the administration of phenylcapsaicin, in a dose dependent manner.

Further, phenylcapsaicin was shown to work selectively on the PDGF pathway since only PDGF-induced proliferation was effectively blocked by phenylcapsaicin, (IC50 at ~1 uM) whereas epithelial proliferation stimulated by VEGF and bFGF was almost not inhibited (IC50>10 uM).

Example 2—Phenylcapsaicin Reduces the Expression of PDGF in Bronchial Epithelial Cells As mentioned above, PDGF has been shown in the literature to be a profibrotic mediator and to play an important role in the pathogenesis of IPF, and it has been shown that inhibition of platelet-derived growth factor signalling attenuates pulmonary fibrosis. Thus, it seems reasonable to assume that blocking the PDGF pathway may be a way of treating IPF.

Method

Cell Culture:

Primary isolated human bronchial epithelial cells (NHBE) (Normal, Human (ATCC® BEAS-2B™)) were cultured up to passage 6. The BEAS-2B cells were cultured in serum-free Ham's F-12 medium supplemented with 5 mg/ml of insulin, 5 mg/ml of transferrin, 20 ng/ml of human EGF, 0.1 Mm dexamethasone, 20 ng/ml of cholera toxin, 30 mg/ml of bovine pituitary extract, and 1 mM retinoic acid.

Clonogenic Cell Survival Assay:

A clonogenic cell survival assay determines the ability of a cell to proliferate indefinitely. The effects of phenylcapsaicin on clonogenic survival of bronchial epithelial cells was investigated by plating the cells with increasing numbers ($10^2$ to $5\times10^4$) in 25 $cm^2$ flasks. SU9518, a known inhibitor for PDGF which has shown the ability to reduce radiation-induced fibroblast and endothelial cell activation, was used as the positive control. The cells were incubated with 0-10 μM of phenylcapsaicin and SU9518 separately in the presence of 10 ng/ml PDGF-AB. The flasks were returned to the incubator for 14 days, after which they were stained with crystal violet. The colonies were counted, and the surviving percentage was determined for clonogenic survival after correcting for plating efficiency.

Proliferation Assay:

Bronchial cells were harvested by trypsinisation at 37° C. and neutralised with trypsin-neutralising solution. A suspension of 50,000 cells in MPM/DMEM was added to 25 ml flasks. The cells were incubated with phenylcapsaicin or SU9518 for 1 hour in cytokine-free medium at standard conditions and incubated for another 72 hours in the presence of final mediums (either with 10 ng/ml PDGF-AB+4 ng/ml FN, or with 2 ng/ml VEGF+4 ng/ml bFGF+4 ng/ml FN). The cells were then dispersed in trypsin, resuspended, and counted in a coulter counter.

Results

Figure 3:
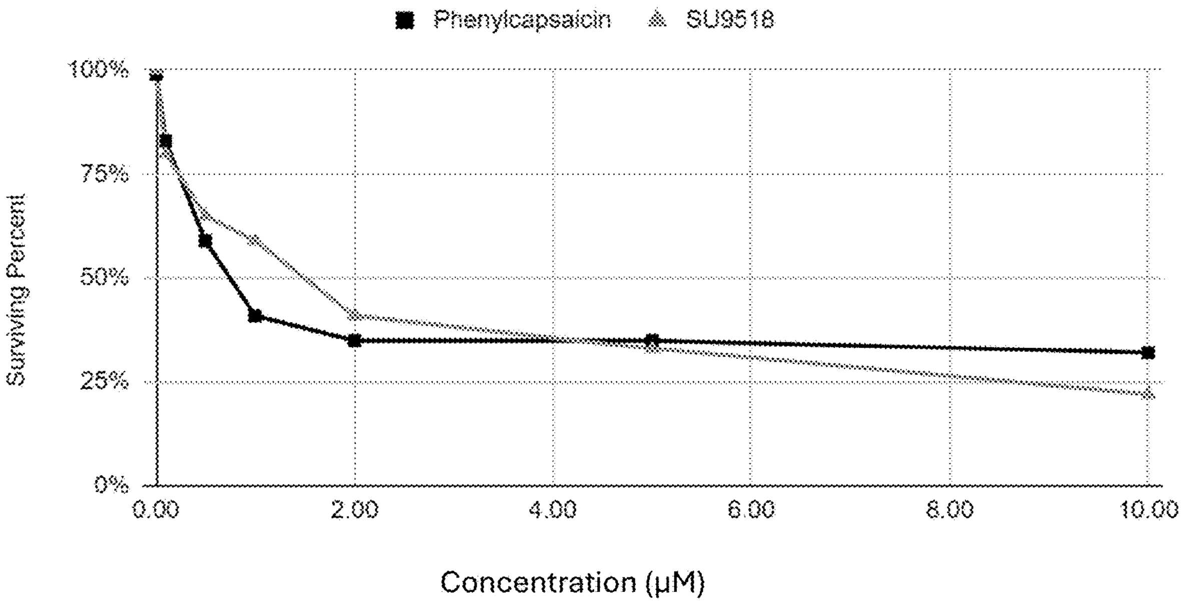
FIG. 3 shows the results from a clonogenic survival assay on survival of human bronchial epithelial cells in the presence of PDGF.

Clonogenic Survival Assay Results:

In the clonogenic survival assay, the inhibitory effects of phenylcapsaicin exhibited a dose-dependent inhibitory effect on survival of human bronchial epithelial cells in the presence of PDGF (-AB isoform, 10 ng/ml). SU9518, a known inhibitor of PDGF signalling, also showed a dose dependent reduction in cell survival. The results are shown in FIG. 3.

Figure 4:
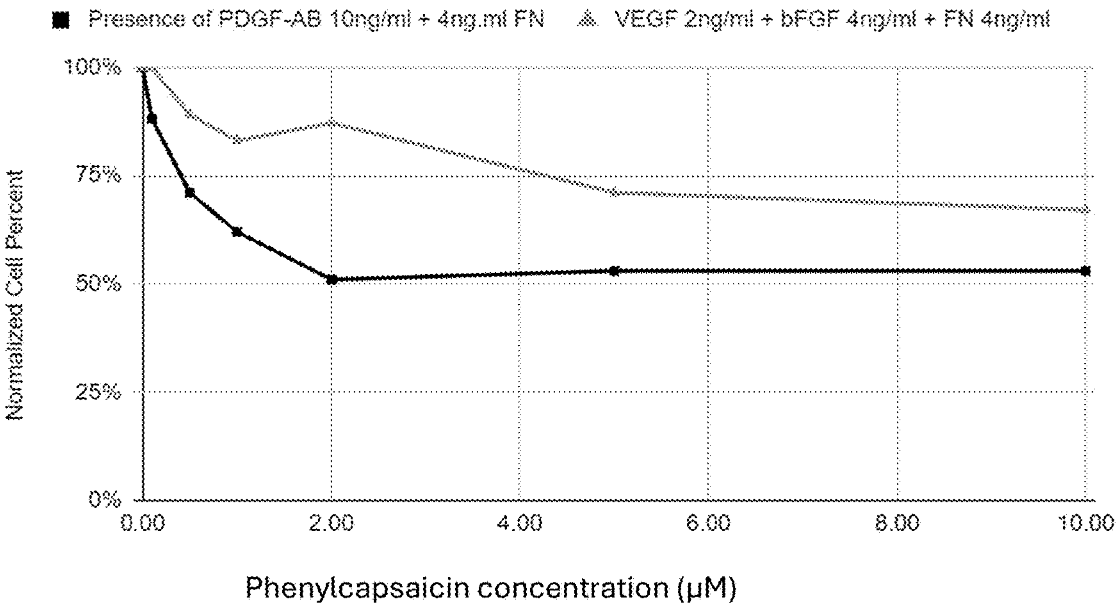
FIG. 4 shows the results from a proliferation assay studying PDGF-stimulated bronchial epithelial proliferation.

Proliferation Assay Results:

To further evaluate the PDGF specificity of phenylcapsaicin, measurements were made of its ability to inhibit PDGF-stimulated bronchial epithelial proliferation as compared to its inhibitory potency to epithelial proliferation stimulated by VEGF+bFGF. As shown in FIG. 4, phenylcapsaicin inhibited 10 ng/ml PDGF-induced epithelial proliferation with an IC50 of ~1 μM. VEGF+bFGF-induced proliferation did not show an IC50 value up to the highest dose (10 uM) of phenylcapsaicin tested.

Discussion/Conclusion

PDGF inhibition is considered a viable mechanistic pathway for the treatment of IPF. Inhibition of PDGF signalling in human bronchial epithelial cells in the presence of phenylcapsaicin showed a reduction in the survival fraction of endothelial cells in a dose dependent manner as seen in the corneal epithelial cells. At 5 μM concentration, phenylcapsaicin reduced the surviving fraction of epithelial cells to 35% versus 33% for the positive control—SU9518. Thus, it can be concluded that PDGF-mediated clonogenic survival of human bronchial epithelial cells is significantly inhibited by the administration of phenylcapsaicin, in a dose dependent manner.

Further, phenylcapsaicin was shown to work selectively on the PDGF pathway, although at a lower selectivity than in corneal cells. PDGF-induced proliferation was effectively blocked by phenylcapsaicin, (IC50 at ~2 uM) whereas epithelial proliferation stimulated by VEGF and bFGF was moderately inhibited (IC75 at ~5 uM).

The results indicate that phenylcapsaicin is a potent inhibitor of PDGF in human lung (bronchial) tissues, and thus a very useful drug candidate against IPF.

Example 3—Evaluation of Capsaicinoids in the Reduction of Expression of PDGF in Bronchial Epithelial Cells Following up the study of Example 2, phenylcapsaicin (2) was tested along with capsaicin (1) and phenylcapsaicin derivatives 3-7 in order to evaluate the ability of each of these compounds to reduce expression of PDGF in bronchial epithelial cells.

1

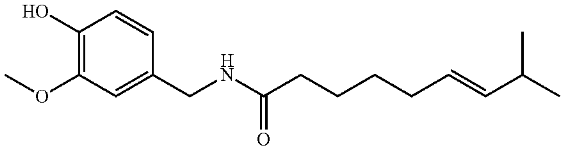

2

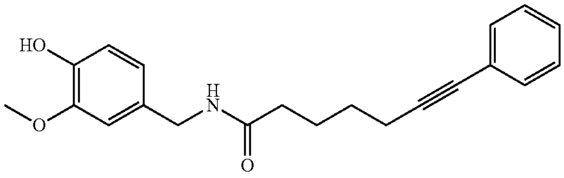

3

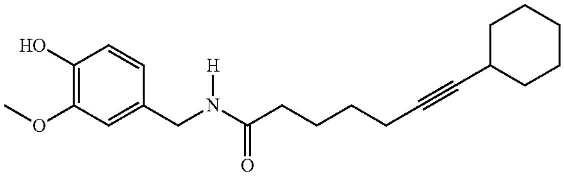

4

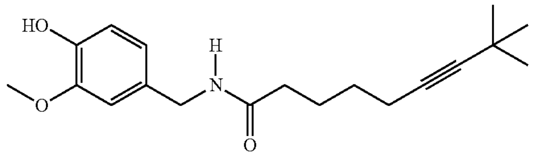

5

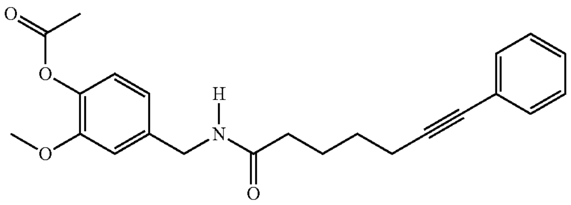

-continued

6

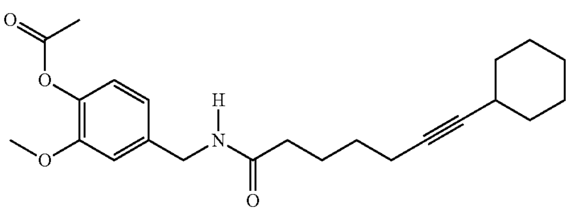

7

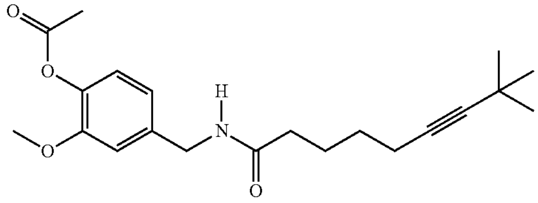

Method

Primary isolated human bronchial epithelial cells (NHBE) were used in this assay sourced from the American Tissue Culture Collection (Normal, Human (ATCC® BEAS-2B™)) and were cultured up to passage 6. The BEAS-2B cells were cultured in serum-free Ham's F-12 medium supplemented with 5 mg/ml of insulin, 5 mg/ml of transferrin, 20 ng/ml of human EGF, 0.1 mM dexamethasone, 20 ng/ml of cholera toxin, 30 mg/ml of bovine pituitary extract, and 1 mM retinoic acid.

Clonogenic Cell Survival Assay:

A clonogenic cell survival assay determines the ability of a cell to proliferate indefinitely. Cells were plated with increasing numbers (102 to $5\times10^4$) in 25 $cm^2$ flasks. SU9518, SU9518, a known inhibitor PDGF that has shown the ability to reduce radiation-induced fibroblast and endothelial cell activation, and phenylcapsaicin were used as positive controls. The cells were incubated with 0-10 μM (3% DMSO aqueous) of phenylcapsaicin, SU9518, and compounds 1 and 3-7 separately in the presence of 10 ng/ml PDGF-AB (Sigma Aldrich). The flasks were returned to the incubator for 14 days, after which they were stained with crystal violet (Sigma Aldrich). The colonies were counted and the surviving percentage was determined for clonogenic survival after correcting for plating efficiency.

Results

Clonogenic Survival Assay Results:

The results from the clonogenic survival assay are shown in Table 1 for each of the tested compounds.

TABLE 1 results from the clonogenic survival assay.
Clonogenic Survival Assay (percent) for compounds 1-7

| Conc (μM) | 2 | SU9518 | 1 | 3 | 4 | 6 | 7 | 5 |
|---|---|---|---|---|---|---|---|---|
| 10.00 | 32% | 22% | 95% | 73% | 91% | 61% | 93% | 20% |
| 5.00 | 35% | 33% | 96% | 71% | 91% | 69% | 94% | 30% |
| 2.00 | 35% | 41% | 96% | 74% | 96% | 64% | 91% | 32% |
| 1.00 | 41% | 59% | 95% | 77% | 97% | 76% | 96% | 45% |
| 0.50 | 59% | 65% | 97% | 83% | 95% | 82% | 96% | 60% |
| 0.10 | 83% | 80% | 97% | 91% | 97% | 89% | 99% | 78% |
| 0.00 | 99% | 100% | 99% | 100% | 99% | 98% | 100% | 100% |

The results strongly indicate that the unsaturated right side of the molecule plays a large role in PDGF inhibition.

Discussion/Conclusion

Inhibition of PDGF signalling in human bronchial epithelial cells in the presence of phenylcapsaicin once again showed a reduction in the survival fraction of endothelial cells in a dose dependent manner.

Five derivatives were also assayed in order to learn about the structure-activity relationship of two key structural elements, the free hydroxy group of the vanillyl ring and the alkynyl benzene phenyl group. Significantly, no inhibition of PDGF was observed for capsaicin in this assay. This primarily indicates the importance of the alkynyl benzene group on the right side of the molecule for PDGF inhibition activity. When this phenyl ring was substituted with a saturated 6-membered ring (compound 3), PDGF inhibition activity dropped significantly, while substitution of the benzene ring with the bulky t-butyl group (compound 4) completely eliminated the PDGF inhibiting activity. Further, it was discovered that acetylation of the vanillyl hydroxy group of phenylcapsaicin (compound 5), gave a significant improvement in PDGF inhibiting activity. More specifically, these results are indicative that the unsaturated right side of the molecule plays a large role in PDGF inhibition. Capsaicin (1) and the t-butyl analogs of PheCap (4 and 7) did not show any PDGF inhibition. The cyclohexyl analogs of PheCap (3 and 6) showed some modest activity, and the —OAc analog of PheCap (5) even showed greater PDGF inhibition than both the parent PheCap (2) and the positive control SU9518.

Example 4—Phenylcapsaicin Analogs—Reduction of Expression of PDGF in Bronchial Epithelial Cells The aim of this third in-vitro assay was to follow-up on the positive results seen on inhibition of PDGF expression in human bronchial epithelial cells with capsaicin and five new synthetic analogs of phenylcapsaicin.

8

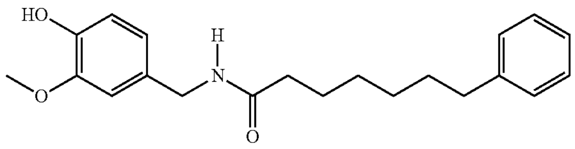

9

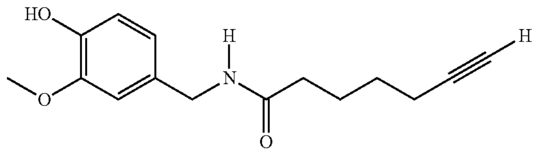

10

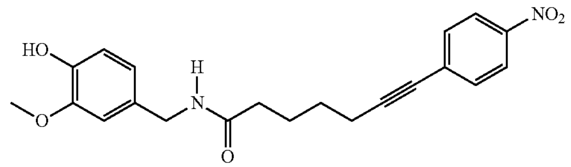

11

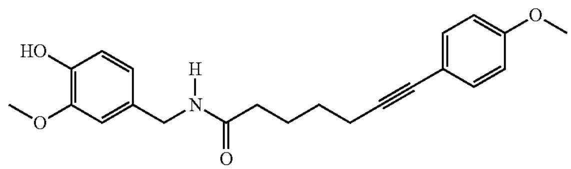

-continued

12

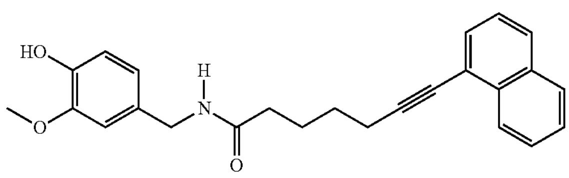

Method:

Primary isolated human bronchial epithelial cells (NHBE) were used in this assay sourced from the American Tissue Culture Collection (Normal, Human (ATCC® BEAS-2B™)) and were cultured up to passage 6. The BEAS-2B cells were cultured in serum-free Ham's F-12 medium supplemented with 5 mg/ml of insulin, 5 mg/ml of transferrin, 20 ng/ml of human EGF, 0.1 mM dexamethasone, 20 ng/ml of cholera toxin, 30 mg/ml of bovine pituitary extract, and 1 mM retinoic acid.

Clonogenic Cell Survival Assay

The effects of Phenylcapsaicin (2) on clonogenic survival of bronchial epithelial cells, by plating the cells with increasing numbers (102 to 5×104) in 25 $cm^2$ flasks were investigated. SU9518* and Phenylcapsaicin were used as positive controls. The cells were incubated with 0-10 μM (3% DMSO aqueous) of Phenylcapsaicin, SU9518, and compounds 8-12 separately in the presence of 10 ng/ml PDGF-AB (Sigma Aldrich). The flasks were returned to the incubator for 14 days, after which they were stained with crystal violet (Sigma Aldrich). The colonies were counted and the surviving percentage was determined for clonogenic survival after correcting for plating efficiency. The synthetic analogs were all calculated at 100% purity for molar concentrations.

Figure 5:
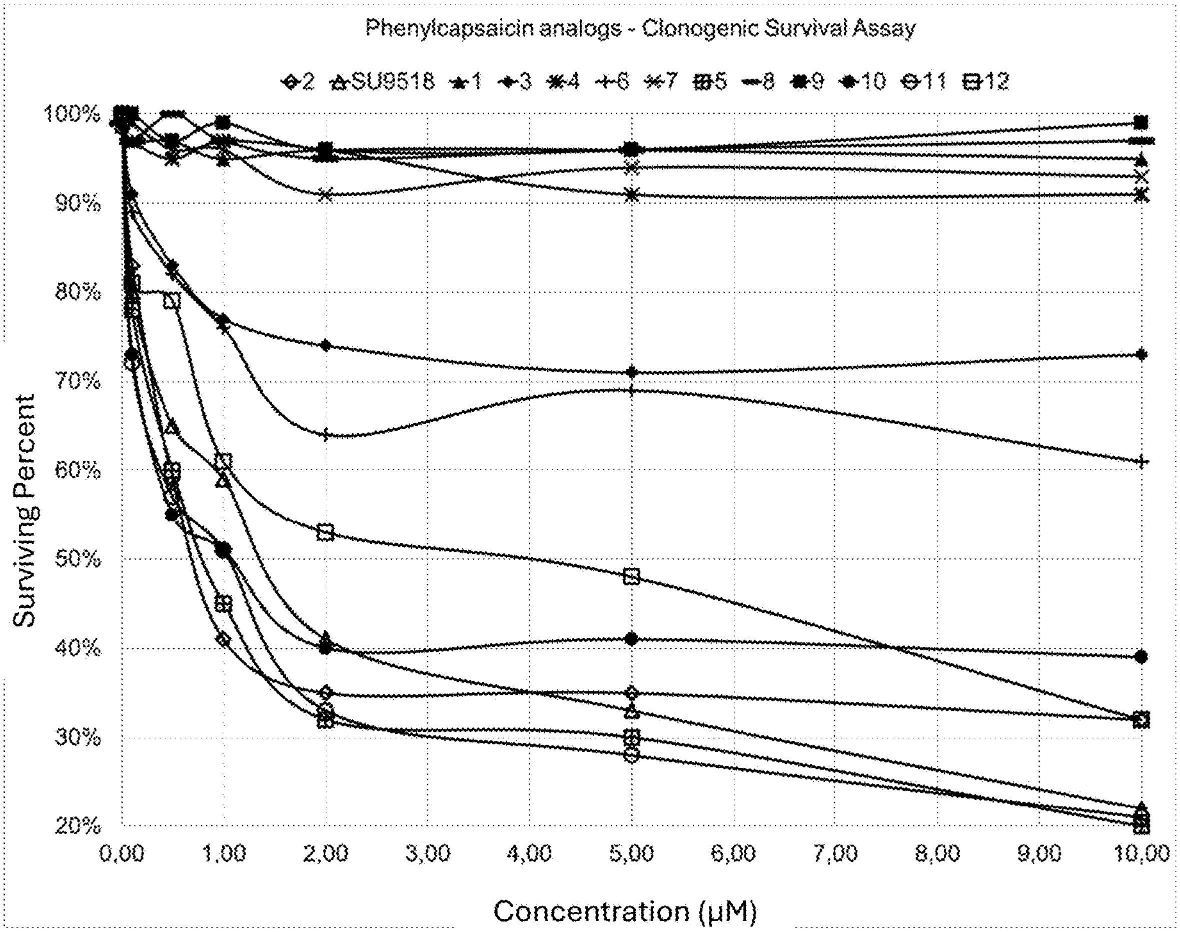
FIG. 5 shows the result from a clonogenic survival assay, study of Examples 3 and 4, testing phenylcapsaicin (2), capsaicin (1), control and analogs.

Results:

The results from the clonogenic survival assay are shown in Table 2 for each of the tested compounds. FIG. 5 further shows the results graphically, including the compounds of both Examples 3 and 4. The X-axis provides the uM concentration, and the Y-axis shows the surviving percent. The resulting graph for each compound 1-12 is provided with a symbol, as denoted at the top of the figure.

TABLE 2 results from the clonogenic survival assay, compounds 1 and 2, SU9518 and 8-12.
Clonogenic Survival Assay (percent) for compounds 8-12

| Conc(uM) | 2 | SU9518 | 1 | 8 | 9 | 10 | 11 | 12 |
|---|---|---|---|---|---|---|---|---|
| 10.00 | 32 | 22 | 95 | 97 | 99 | 39 | 21 | 32 |
| 5.00 | 35 | 33 | 96 | 96 | 96 | 41 | 28 | 48 |
| 2.00 | 35 | 41 | 96 | 95 | 96 | 40 | 33 | 53 |
| 1.00 | 41 | 59 | 95 | 97 | 99 | 51 | 51 | 61 |
| 0.50 | 59 | 65 | 98 | 100 | 97 | 55 | 57 | 79 |
| 0.10 | 83 | 80 | 97 | 97 | 100 | 73 | 72 | 81 |
| 0.00 | 99 | 100 | 99 | 99 | 100 | 99 | 100 | 100 |

Compound 8, the saturated side-chain analog of phenylcapsaicin (2) and 9, the desphenyl analog of phenylcapsaicin, did not show any reduction in clonogenic cell survival.

Compound 12, the naphthalene analog of phenylcapsaicin and 10, the 4-nitrophenyl analog of phenylcapsaicin, showed similar cell survival percent as the parent phenylcapsaicin.

Compound 11, the 4-methoxyphenyl analog of phenylcapsaicin showed a higher reduction than the lead phenylcapsaicin in this cell survival. This reduction was equivalent to the activity seen with the acetylated guaiacol analog, 5, and the SU9518 positive control.

Inhibition of PDGF signaling in human bronchial epithelial cells in the presence of phenylcapsaicin once again showed a reduction in the survival fraction of endothelial cells in a dose dependent manner. The five analogs were also assayed to develop a SAR on two key structural elements, the free hydroxyl group on the left hand guaiacol ring and the alkynyl benzene on the right hand side of the molecule. Significantly, no inhibition of PDGF was observed for Capsaicin in this assay. This primarily indicates the importance of the alkynyl benzene group on the right side of the molecule for PDGF inhibition activity. When the benzene ring was substituted with a saturated 6-membered ring (cyclohexyl), PDGF inhibition activity dropped significantly while substitution of the benzene ring with a bulky alkyl group ((t-butyl) completely eliminated the PDGF inhibiting activity. Surprisingly, acetylation of the guaiacol hydroxyl group in PheCap (5)) gave a significant improvement in PDGF inhibiting activity. Furthermore, the PDGF inhibiting activity was further improved by an alkoxy group, such as a 4-OMe substitution, on the side chain phenyl ring, as seen for compound 11.

Thus, it can be concluded that the inhibiton of PDGF-mediated clonogenic survival of human bronchial epithelial cells is significantly increased by acetylation of the guaiacol hydroxyl group, and an unsaturated ring at the right-hand terminus of the PheCap structure is also favourable for PDGF inhibition.

The invention claimed is:

1. A method for the treatment of idiopathic pulmonary fibroses (IPF) of a subject, the method comprising the step of administering an effective amount of a compound of formula II, or a pharmaceutically acceptable salt or solvate thereof,

II

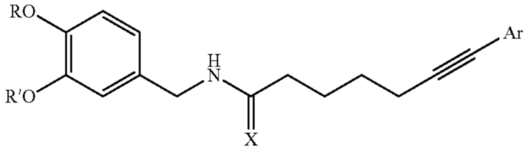

wherein

X is selected from oxygen and sulphur;

Ar denotes an aryl group optionally containing one or more nitrogen, oxygen, or sulphur atoms, and optionally substituted in any one or more positions with one or more identical or different substituents selected from the group of nitro, trifluoromethyl, $C_1$-$C_6$ straight chain and branched alkoxy, $C_1$-$C_6$ straight chain and branched alkyl;

R' is selected from the group of hydrogen, $C_1$-$C_6$ straight chain or branched alkyl; and R is selected from the group of hydrogen; $C_1$-$C_6$ straight chain and branched alkyl, alkenyl, and alkynyl; $C_3$-$C_6$ cycloalkyl; acyl groups $COR^1$ wherein $R^1$ is selected from the group comprising or consisting of $C_1$-$C_6$ straight chain and branched alkyl, alkenyl, and alkynyl, $C_3$-$C_6$ cycloalkyl and phenyl.

2. The method according to claim 1, wherein X is oxygen.

3. The method according to claim 1, wherein Ar is an unsubstituted or substituted phenyl or naphthyl group.

4. The method according to claim 1, wherein the one or more substituents are selected from the group of nitro and $C_1$-$C_6$ straight chain and branched alkoxy.

5. The method according to claim 1, wherein R' is H or methyl, and R is H or an acyl group $COR^1$ wherein $R^1$ is a $C_1$-$C_6$ straight chain or branched alkyl.

6. The method according to claim 1, wherein R' is methyl and R is acetyl.

7. A method for the treatment of idiopathic pulmonary fibroses (IPF) of a subject, the method comprising the step of administering a composition comprising the compound or pharmaceutically acceptable salt or solvate thereof according to claim 1 to the subject.

8. The method according to claim 7, wherein the composition is formulated for inhalation.

9. The method according to claim 1, wherein the method comprises the step of administering the compound to a subject by pulmonal, oral, and/or intravenous administration.

10. The method according to claim 1, wherein the method comprises the step of administering the compound to a subject by inhalation.

11. A kit comprising i) the compound according to claim 1; and ii) an inhaler.

12. The method according to claim 7, wherein the method comprises the step of administering the composition to a subject by pulmonal, oral, and/or intravenous administration.

13. The method according to claim 7 wherein the method comprises the step of administering the composition to a subject by inhalation.

14. A kit comprising i) the composition according to claim 7; and ii) an inhaler.

* * * * *